United States Patent
Morant

(10) Patent No.: US 10,227,614 B2
(45) Date of Patent: *Mar. 12, 2019

(54) POLYPEPTIDES HAVING BETA-GLUCOSIDASE ACTIVITY, BETA-XYLOSIDASE ACTIVITY, OR BETA-GLUCOSIDASE AND BETA-XYLOSIDASE ACTIVITY AND POLYNUCLEOTIDES ENCODING SAME

(71) Applicants: NOVOZYMES A/S, Bagsvaerd (DK); NOVOZYMES, INC., Davis, CA (US)

(72) Inventor: Marc Morant, Copenhagen (DK)

(73) Assignees: NOVOZYMES A/S, Bagsvaerd (DK); NOVOZYMES, INC., Davis, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/400,361

(22) Filed: Jan. 6, 2017

(65) Prior Publication Data

US 2017/0114372 A1    Apr. 27, 2017

Related U.S. Application Data

(63) Continuation of application No. 14/357,902, filed as application No. PCT/US2012/065568 on Nov. 16, 2012, now Pat. No. 9,562,222.

(60) Provisional application No. 61/561,472, filed on Nov. 18, 2011.

(51) Int. Cl.

| | |
|---|---|
| *C12P 7/14* | (2006.01) |
| *C12N 15/52* | (2006.01) |
| *C12N 9/42* | (2006.01) |
| *C12N 9/24* | (2006.01) |
| *C12P 19/02* | (2006.01) |
| *C12P 19/14* | (2006.01) |
| *C12P 7/10* | (2006.01) |
| *C12P 7/16* | (2006.01) |
| *C12P 7/20* | (2006.01) |

(52) U.S. Cl.
CPC .............. *C12P 7/14* (2013.01); *C12N 9/2437* (2013.01); *C12N 9/2445* (2013.01); *C12N 9/2482* (2013.01); *C12N 15/52* (2013.01); *C12P 7/10* (2013.01); *C12P 7/16* (2013.01); *C12P 7/20* (2013.01); *C12P 19/02* (2013.01); *C12P 19/14* (2013.01); *C12Y 302/01008* (2013.01); *C12Y 302/01021* (2013.01); *C12P 2203/00* (2013.01); *Y02E 50/16* (2013.01); *Y02P 20/52* (2015.11)

(58) Field of Classification Search
None
See application file for complete search history.

(56) References Cited

U.S. PATENT DOCUMENTS

| 8,486,683 B2 | 7/2013 | Scott |
| 8,709,776 B2 | 4/2014 | Morant |
| 8,715,994 B2 | 5/2014 | Morant |
| 8,715,995 B2 | 5/2014 | Morant |
| 9,562,222 B2 * | 2/2017 | Morant ............ C12Y 302/0102 |
| 2007/0021597 A1 | 1/2007 | Edwards |
| 2008/0201805 A1 | 8/2008 | Krogh |
| 2014/0201871 A1 | 7/2014 | Morant |

FOREIGN PATENT DOCUMENTS

| WO | 98003172 A1 | 5/1988 |
| WO | 0224926 A1 | 3/2002 |
| WO | 2009108941 A2 | 9/2009 |
| WO | 2010055495 A2 | 5/2010 |

OTHER PUBLICATIONS

Copeland et al, 2007—Uniprot Access No. A8GHK1.
Guo et al, 2004, PNAS 101 (25), 9205-9210.
Martin et al, 2008—Swissprot Access No. B0D3B6.
Martin et al, 2008—Swissprot Access No. B0D734.
Martin et al, 2009—Swissprot Access No. B8P3Z6.
Mondego et al, 2010—Swissprot Access No. E2LXM8.
Misra et al, 1986—Uniprot Access No. P04131.
McClean et al, 1998, Nucl Acid Hybrid NDSU 731, 1-6.
Machida et al, 2006—Uniprot Access No. Q2U8V9.
Pozzo et al, 2010, J Mol Biol 397, 724-739.
Eastwood et al, 2011—Uniport Access F8NLG7.
Martinez et al, 2009—Swissprot Access No. B8PDN5.
Rasmussen et al, Biotechnol Bioeng 94(5), 869-876.
Fedorova et al, 2007, UniProt Accession No. B8MNC6.
WO 2009-108941 A2—EBI Accession No. AXR39039.
Murray et al, 2004, Prot Expres Purif 38(2), 248-257.
Hong et al, 2006, Appl Microbiol Biotechnol 73(1), 80-88.
Fedorova et al, 2010, EBI Accession No. A1DCV5.
Nierman et al, 2010, EBI Accession No. Q4WGT3.

* cited by examiner

*Primary Examiner* — Brent T Page
(74) *Attorney, Agent, or Firm* — Robert Starnes

(57) ABSTRACT

The present invention relates to isolated polypeptides having beta-glucosidase activity, beta-xylosidase activity, or beta-glucosidase and beta-xylosidase activity and isolated polynucleotides encoding the polypeptides. The invention also relates to nucleic acid constructs, vectors, and host cells comprising the polynucleotides as well as methods of producing and using the polypeptides.

27 Claims, No Drawings
Specification includes a Sequence Listing.

POLYPEPTIDES HAVING BETA-GLUCOSIDASE ACTIVITY, BETA-XYLOSIDASE ACTIVITY, OR BETA-GLUCOSIDASE AND BETA-XYLOSIDASE ACTIVITY AND POLYNUCLEOTIDES ENCODING SAME

CROSS-REFERENCE TO RELATED APPLICATIONS

This application is a continuation of U.S. application Ser. No. 14/357,902 filed May 13, 2014, now U.S. Pat. No. 9,562,222, which is a 35 U.S.C. § 371 national application of PCT/US2012/065568 filed Nov. 16, 2012, which claims priority or the benefit under 35 U.S.C. § 119 of U.S. Provisional Application No. 61/561,472 filed Nov. 18, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having beta-glucosidase activity, beta-xylosidase activity, or beta-glucosidase and beta-xylosidase activity and polynucleotides encoding the polypeptides. The invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art for polypeptides having beta-glucosidase activity, beta-xylosidase activity, or beta-glucosidase and beta-xylosidase activity with improved properties for use in the degradation of cellulosic and xylan-containing materials.

The present invention provides new polypeptides having beta-glucosidase activity, beta-xylosidase activity, or beta-glucosidase and beta-xylosidase activity and polynucleotides encoding the polypeptides.

The polypeptides according to the present invention share 59.16% identity (excluding gaps) to the deduced maturated amino acid sequence of a GH3 family protein from *Talaromyces stipitatus* (SwissProt accession number B8MNC6), 82.58% identity (excluding gaps) to the deduced maturated amino acid sequence of a GH3 family protein from *Thermoascus aurantiacus* (SwissProt accession number Q4U4W7), 78.55% identity (excluding gaps) to the deduced maturated amino acid sequence of a GH3 family protein from *Thermoascus aurantiacus* var. *levisporus* (SwissProt accession number A9UFC6), and 82.87% identity (excluding gaps) to the maturated deduced amino acid sequence of a GH3 family protein from *Neosartorya fischeri* (SwissProt accession number A1DCV5) respectively.

SUMMARY OF THE INVENTION

The present invention relates to isolated polypeptides having beta-glucosidase activity, beta-xylosidase activity, or beta-glucosidase and beta-xylosidase activity selected from the group consisting of:

(a) a polypeptide having at least 65% sequence identity to the mature polypeptide of SEQ ID NO: 2, a polypeptide having at least 85% sequence identity to the mature SEQ ID NO: 4, a polypeptide having at least 80% sequence identity to the mature SEQ ID NO: 6, or a polypeptide having at least 85% sequence identity to the mature SEQ ID NO: 8;

(b) a polypeptide encoded by a polynucleotide that hybridizes under at least medium stringency conditions with (i) the mature polypeptide coding sequence of SEQ ID NO: 1 or the cDNA sequence thereof, or (ii) the full-length complement of (i);

(c) a polypeptide encoded by a polynucleotide that hybridizes under at least high stringency conditions with (i) the mature polypeptide coding sequence of SEQ ID NO: 3 or the cDNA sequence thereof, the mature polypeptide coding sequence of SEQ ID NO: 5 or the cDNA sequence thereof, or the mature polypeptide coding sequence of SEQ ID NO: 7 or the cDNA sequence thereof, or (ii) the full-length complements of (i);

(d) a polypeptide encoded by a polynucleotide having at least 65% sequence identity to the mature polypeptide coding sequence of SEQ ID NO: 1 or the cDNA sequence thereof, a polypeptide encoded by a polynucleotide having at least 85% sequence identity to the mature polypeptide coding sequence of SEQ ID NO: 3 or the cDNA sequence thereof, a polypeptide encoded by a polynucleotide having at least 80% sequence identity to the mature polypeptide coding sequence of SEQ ID NO: 5 or the cDNA sequence thereof, or a polypeptide encoded by a polynucleotide having at least 85% sequence identity to the mature polypeptide coding sequence of SEQ ID NO: 7 or the cDNA sequence thereof;

(e) a variant of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions; and (f) a fragment of the polypeptide of (a), (b), (c), (d) or (e) that has beta-glucosidase activity, beta-xylosidase activity, or beta-glucosidase and beta-xylosidase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention.

The present invention also relates to a polynucleotide encoding a signal peptide comprising or consisting of amino acids 1 to 22 of SEQ ID NO: 2, amino acids 1 to 22 of SEQ ID NO: 4, amino acids 1 to 19 of SEQ ID NO: 6, amino acids 1 to 19 of SEQ ID NO: 8, which is operably linked to a gene encoding a protein, wherein the gene is foreign to the polynucleotide encoding the signal peptide; nucleic acid constructs, expression vectors, and recombinant host cells comprising the polynucleotides; and methods of producing a protein.

Definitions

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 micromole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 microliters for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 micromole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 micromole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-glucosidase activity of the mature polypeptide of SEQ ID NO: 2, SEQ ID NO: 4, SEQ ID NO: 6, or SEQ ID NO: 8.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 micromole of p-nitrophenolate anion produced per minute at 40° C., pH 5 from 1 mM p-nitrophenyl-beta-D-xyloside as substrate in 100 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-xylosidase activity of the mature polypeptide of SEQ ID NO: 2, SEQ ID NO: 4, SEQ ID NO: 6, or SEQ ID NO: 8.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-beta-D-lactoside.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., 2006, Outlook for cellulase improvement: Screening and selection strategies, *Biotechnology Advances* 24: 452-481. Total cellulolytic activity is usually measured using insoluble substrates, including Whatman N° 1 filter paper, microcrystalline cellulose, bacterial cellulose, algal cellulose, cotton, pretreated lignocellulose, etc. The most common total cellulolytic activity assay is the filter paper assay using Whatman N° 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM MnSO$_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 micromole of p-nitrophenolate anion per minute at pH 5, 25° C.

Fragment: The term "fragment" means a polypeptide having one or more (e.g., several) amino acids deleted from the amino and/or carboxyl terminus of a mature polypeptide; wherein the fragment has beta-glucosidase activity, beta-xylosidase activity, or beta-glucosidase and beta-xylosidase activity. In one aspect, a fragment contains at least 341 amino acid residues, e.g., amino acid residues 150 to 490 of SEQ ID NO: 2. In another aspect, a fragment contains at least 329 amino acid residues, e.g., at least amino acid residues 37 to 365 of SEQ ID NO: 4. In another aspect, a fragment contains at least 350 amino acid residues, e.g., at least amino acid residues 21 to 370 of SEQ ID NO: 6. In another aspect, a fragment contains at least 317 amino acid residues, e.g., at least amino acid residues 25 to 341 of SEQ ID NO: 8.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 23 to 950 of SEQ ID NO: 2 based on the SignalP program (Nielsen et al., 1997, *Protein Engineering* 10: 1-6) that predicts amino acids 1 to 22 of SEQ ID NO: 2 are a signal peptide. In another aspect, the mature polypeptide is amino acids 23 to 868 of SEQ ID NO: 4 based on the SignalP program that predicts amino acids 1 to 22 of SEQ ID NO: 4 are a signal peptide. In another aspect, the mature polypeptide is amino acids 20 to 860 of SEQ ID NO: 6 based on the SignalP program that predicts amino acids 1 to 19 of SEQ ID NO: 6 are a signal peptide. In another aspect, the mature polypeptide is amino acids 20 to 737 of SEQ ID NO: 8 based on the SignalP program that predicts amino acids 1 to 19 of SEQ ID NO: 8 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-glucosidase activity, beta-xylosidase activity, or beta-glucosidase and beta-xylosidase activity. In one aspect, the mature polypeptide coding sequence is nucleotides 67 to 3025 of SEQ ID NO: 1 based on the SignalP program (Nielsen et al., 1997, supra) that predicts nucleotides 1 to 66 of SEQ ID NO: 1 encode a signal peptide. In another aspect, the mature polypeptide coding sequence is the cDNA sequence contained in nucleotides 67 to 3025 of SEQ ID NO: 1. In another aspect the mature polypeptide coding sequence is nucleotides 67 to 281, 350 to 460, 516 to 792, 842 to 3025 of SEQ ID NO: 1. In another aspect, the mature polypeptide coding sequence is nucleotides 67 to 2850 of SEQ ID NO: 3 based on the SignalP program that predicts nucleotides 1 to 66 of SEQ ID NO: 3 encode a signal peptide. In another aspect, the mature polypeptide coding sequence is the cDNA sequence contained in nucleotides 67 to 2850 of SEQ ID NO: 3. In another aspect the mature polypeptide coding sequence is nucleotides 67 to 225, 286 to 514, 576 to 898, 952 to 1203, 1273 to 2850 of SEQ ID NO: 3. In another aspect, the mature polypeptide coding sequence is nucleotides 58 to 3041 of SEQ ID NO: 5 based on the SignalP program that predicts nucleotides 1 to 57 of SEQ ID NO: 5 encode a signal peptide. In another aspect, the mature polypeptide coding sequence is the cDNA sequence contained in nucleotides 58 to 3041 of SEQ ID NO: 5. In another aspect the mature polypeptide coding sequence is nucleotides 58 to 60, 231 to 370, 448 to 545, 608 to 1799, 1885 to 2743, 2808 to 3041 of SEQ ID NO: 5. In another aspect, the mature polypeptide coding sequence is nucleotides 58 to 2465 of SEQ ID NO: 7 based on the SignalP program that predicts nucleotides 1 to 57 of SEQ ID NO: 7 encode a signal peptide. In another aspect, the mature polypeptide coding sequence is the cDNA sequence contained in nucleotides 58 to 2465 of SEQ ID NO: 7. In another aspect the mature polypeptide coding sequence is nucleotides 58 to 528, 596 to 1312, 1369 to 1523, 1582 to 1988, 2059 to 2465 of SEQ ID NO: 7.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 02/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-glucosidase activity, beta-xylosidase activity, or beta-glucosidase and beta-xylosidase activity. In one aspect, a subsequence contains at least the polynucleotides encoding the fragments according to the invention or the cDNA thereof.

Variant: The term "variant" means a polypeptide having beta-glucosidase activity, beta-xylosidase activity, or beta-glucosidase and beta-xylosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67. In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, Recent progress in the assays of xylanolytic enzymes, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann et al., 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, Anal. Biochem 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Beta-Glucosidase Activity, Beta-Xylosidase Activity, or Beta-Glucosidase and Beta-Xylosidase Activity In an embodiment, the present invention relates to isolated polypeptides having a sequence identity to the mature polypeptide of SEQ ID NO: 2 of at least 65%, e.g., at least 70%, at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity.

In another embodiment, the present invention relates to isolated polypeptides having a sequence identity to the mature polypeptide of SEQ ID NO: 4 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity.

In another embodiment, the present invention relates to isolated polypeptides having a sequence identity to the mature polypeptide of SEQ ID NO: 6 of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity.

In another embodiment, the present invention relates to isolated polypeptides having a sequence identity to the mature polypeptide of SEQ ID NO: 8 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity.

In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, SEQ ID NO: 8.

A polypeptide of the present invention preferably comprises or consists of the amino acid sequence of SEQ ID NO: 2, SEQ ID NO: 4, SEQ ID NO: 6, or SEQ ID NO: 8; or an allelic variant thereof; or is a fragment thereof having beta-glucosidase activity, beta-xylosidase activity, or beta-glucosidase and beta-xylosidase activity. In another aspect, the polypeptide comprises or consists of the mature polypeptide of SEQ ID NO: 2, SEQ ID NO: 4, SEQ ID NO: 6, SEQ ID NO: 8. In another aspect, the polypeptide comprises or consists of amino acids 23 to 950 of SEQ ID NO: 2. In another aspect, the polypeptide comprises or consists of amino acids 23 to 868 of SEQ ID NO: 4. In another aspect, the polypeptide comprises or consists of amino acids 20 to 860 of SEQ ID NO: 6. In another aspect, the polypeptide comprises or consists of amino acids 20 to 737 of SEQ ID NO: 8. In another embodiment, the present invention relates to isolated polypeptides having beta-glucosidase activity, beta-xylosidase activity, or beta-glucosidase and beta-xylosidase activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof, or (ii) the full-length complement of (i) (J. Sambrook, E. F. Fritsch, and T. Maniatis, 1989, *Molecular Cloning, A Laboratory Manual*, 2d edition, Cold Spring Harbor, N.Y.).

In particular the present invention relates to isolated polypeptides having beta-glucosidase activity, beta-xylosidase activity, or beta-glucosidase and beta-xylosidase activity that are encoded by polynucleotides that hybridize under at least medium stringency conditions with (i) the mature polypeptide coding sequence of SEQ ID NO: 1 or the cDNA sequence thereof, or (ii) the full-length complement of (i); or to isolated polypeptides having beta-glucosidase activity, beta-xylosidase activity, or beta-glucosidase and beta-xylosidase activity that are encoded by polynucleotides that hybridize under at least high stringency conditions with (i) the mature polypeptide coding sequence of SEQ ID NO: 3 or the cDNA sequence thereof, SEQ ID NO: 5 or the cDNA sequence thereof, or SEQ ID NO: 7 or the cDNA sequence thereof, or (ii) the full-length complements of (i).

In particular the present invention relates to isolated polypeptides having beta-glucosidase activity, beta-xylosidase activity, or beta-glucosidase and beta-xylosidase activity that are encoded by polynucleotides that hybridize under at least medium-high stringency conditions with (i) the mature polypeptide coding sequence of SEQ ID NO: 1 or the cDNA sequence thereof, or (ii) the full-length complement of (i); or to isolated polypeptides having beta-glucosidase activity, beta-xylosidase activity, or beta-glucosidase and beta-xylosidase activity that are encoded by polynucleotides that hybridize under at least high stringency conditions with (i) the mature polypeptide coding sequence of SEQ ID NO: 3 or the cDNA sequence thereof, SEQ ID NO: 5 or the cDNA sequence thereof, or SEQ ID NO: 7 or the cDNA sequence thereof, or (ii) the full-length complements of (i).

In particular the present invention relates to isolated polypeptides having beta-glucosidase activity, beta-xylosidase activity, or beta-glucosidase and beta-xylosidase activity that are encoded by polynucleotides that hybridize under at least high stringency conditions with (i) the mature polypeptide coding sequence of SEQ ID NO: 1 or the cDNA sequence thereof, or (ii) the full-length complement of (i); or to isolated polypeptides having beta-glucosidase activity, beta-xylosidase activity, or beta-glucosidase and beta-xylosidase activity that are encoded by polynucleotides that hybridize under at least high stringency conditions with (i) the mature polypeptide coding sequence of SEQ ID NO: 3 or the cDNA sequence thereof, SEQ ID NO: 5 or the cDNA sequence thereof, or SEQ ID NO: 7 or the cDNA sequence thereof, or (ii) the full-length complements of (i).

In particular the present invention relates to isolated polypeptides having beta-glucosidase activity, beta-xylosidase activity, or beta-glucosidase and beta-xylosidase activity that are encoded by polynucleotides that hybridize under at least very high stringency conditions with (i) the mature polypeptide coding sequence of SEQ ID NO: 1 or the cDNA sequence thereof, or (ii) the full-length complement of (i); or to isolated polypeptides having beta-glucosidase activity, beta-xylosidase activity, or beta-glucosidase and beta-xylosidase activity that are encoded by polynucleotide that hybridizes under at least high stringency conditions with (i) the mature polypeptide coding sequence of SEQ ID NO: 3 or the cDNA sequence thereof, SEQ ID NO: 5 or the cDNA sequence thereof, or SEQ ID NO: 7 or the cDNA sequence thereof, or (ii) the full-length complements of (i).

The polynucleotide of SEQ ID NO: 1, SEQ ID NO: 3, SEQ ID NO: 5, or SEQ ID NO: 7, or a subsequence thereof, as well as the amino acid sequence of SEQ ID NO: 2, SEQ ID NO: 4, SEQ ID NO: 6, or SEQ ID NO: 8, or a fragment thereof, may be used to design nucleic acid probes to identify and clone DNA encoding polypeptides having beta-glucosidase activity, beta-xylosidase activity, or beta-glucosidase and beta-xylosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having beta-glucosidase activity, beta-xylosidase activity, or beta-glucosidase and beta-xylosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, or SEQ ID NO: 7, or a subsequence thereof, the carrier material is used in a Southern blot.

For purposes of the present invention, hybridization indicates that the polynucleotide hybridizes to a labeled nucleic acid probe corresponding to SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof; the mature polypeptide coding sequence of SEQ ID NO: 1, SEQ ID NO: 3, SEQ ID NO: 5, SEQ ID NO: 7; the full-length complement thereof; or a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof. In another aspect, the nucleic acid probe is nucleotides 67 to 3025 of SEQ ID NO: 1, nucleotides 67 to 2850 of SEQ ID NO: 3, nucleotides 58 to 3041 of SEQ ID NO: 5, or nucleotides 58 to 2465 of SEQ ID NO: 7. In another aspect, the nucleic acid probe is a polynucleotide that encodes the polypeptide of SEQ ID NO: 2, SEQ ID NO: 4, SEQ ID NO: 6, or SEQ ID NO: 8, or the mature polypeptide thereof; or a fragment thereof. In another aspect, the nucleic acid probe is SEQ ID NO: 1 or the cDNA sequence thereof, SEQ ID NO: 3 or the cDNA sequence thereof, SEQ ID NO: 5 or the cDNA sequence thereof, SEQ ID NO: 7 or the cDNA sequence thereof.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 1 or the cDNA sequence thereof of at least 65%, e.g., at least 70%, at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 3 or the cDNA sequence thereof of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 5 or the cDNA sequence thereof of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 7 or the cDNA sequence thereof of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, or SEQ ID NO: 8 is not more than 10, e.g., 1, 2, 3, 4, 5, 6, 7, 8, 9, or 10. The, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for beta-glucosidase activity, beta-xylosidase activity, or beta-glucosidase and beta-xylosidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512;

Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Beta-Glucosidase Activity, Beta-Xylosidase Activity, or Beta-Glucosidase and Beta-Xylosidase Activity A polypeptide having beta-glucosidase activity, beta-xylosidase activity, or beta-glucosidase and beta-xylosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

Particularly the polypeptide may be a *Talaromyces* polypeptide.

In another aspect, the polypeptide is a *Talaromyces leycettanus* polypeptide, e.g., a polypeptide obtained from strain CBS398.68.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus aculeatus*, or a related organism and thus, for example, may be an allelic or species variant of the polypeptide encoding region of the polynucleotide.

In another embodiment, the present invention relates to isolated polynucleotides comprising or consisting of polynucleotides having a degree of sequence identity to the mature polypeptide coding sequence of SEQ ID NO: 1 or the cDNA sequence thereof, of at least 65%, e.g. at least 70%, at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

In another embodiment, the present invention relates to isolated polynucleotides comprising or consisting of polynucleotides having a degree of sequence identity to the mature polypeptide coding sequence of SEQ ID NO: 3 or the cDNA sequence thereof, of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

In another embodiment, the present invention relates to isolated polynucleotides comprising or consisting of polynucleotides having a degree of sequence identity to the mature polypeptide coding sequence of SEQ ID NO: 5 or the cDNA sequence thereof, of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

In another embodiment, the present invention relates to isolated polynucleotides comprising or consisting of polynucleotides having a degree of sequence identity to the mature polypeptide coding sequence of SEQ ID NO: 7 or the cDNA sequence thereof, of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or the cDNA sequence thereof, SEQ ID NO: 3 or the cDNA sequence thereof, SEQ ID NO: 5 or the cDNA sequence thereof, or SEQ ID NO: 7 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In another embodiment, the present invention relates to isolated polynucleotides encoding polypeptides of the present invention, which hybridize under low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, or SEQ ID NO: 7 or the cDNA sequence thereof, or (ii) the full-length complement of (i); or allelic variants and subsequences thereof (Sambrook et al., 1989, supra), as defined herein.

In one aspect, the polynucleotide comprises or consists of SEQ ID NO: 1, SEQ ID NO: 3, SEQ ID NO: 5, or SEQ ID NO: 7; or the mature polypeptide coding sequence thereof; or a subsequence thereof that encodes a fragment having beta-glucosidase activity, beta-xylosidase activity, or beta-glucosidase and beta-xylosidase activity.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phiebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium suiphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phiebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Talaromyces* or *Penicillium*. In another aspect, the cell is *Talaromyces leycettanus*. In another aspect, the cell is *Talaromyces leycettanus* strain CBS398.68.

The present invention also relates to methods of producing a polypeptide of the present invention, comprising: (a) cultivating a recombinant host cell of the present invention under conditions conducive for production of the polypeptide; and (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the beta-glucosidase activity, beta-xylosidase activity, or beta-glucosidase and beta-xylosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The compositions may be prepared in accordance with methods known in the art and may be in the form of a liquid or a dry composition. The polypeptide to be included in the composition may be stabilized in accordance with methods known in the art.

The compositions may be a fermentation broth formulation or a cell composition, as described herein. Consequently, the present invention also relates to fermentation broth formulations and cell compositions comprising a polypeptide having beta-glucosidase activity, beta-xylosidase activity, or beta-glucosidase and beta-xylosidase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3 (4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextnnases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having beta-glucosidase activity, beta-xylosidase activity, or beta-glucosidase and beta-xylosidase activity, or compositions thereof.

The present invention also relates to processes for degrading a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd et al., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, Optimal control in fed-batch reactor for the cellobiose hydrolysis, *Acta Scientiarum. Technology* 25: 33-38; Gusakov and Sinitsyn, 1985, Kinetics of the enzymatic hydrolysis of cellulose: 1. A mathematical model for a batch reactor process, *Enz. Microb. Technol.* 7: 346-352), an attrition reactor (Ryu and Lee, 1983, Bioconversion of waste cellulose by using an attrition bioreactor, *Biotechnol. Bioeng.* 25: 53-65), or a reactor with intensive stirring induced by an electromagnetic field (Gusakov et al., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, presoaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Application Publication No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (Apr.), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, Biotechnol. Bioeng. 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Application Publication No. 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt. %, e.g., 20-70 wt. % or 30-60 wt. %, such as around 40 wt. %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having beta-glucosidase activity, beta-xylosidase activity, or beta-glucosidase and beta-xylosidase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt. %, e.g., about 10 to about 40 wt. % or about 20 to about 30 wt. %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having beta-glucosidase activity, beta-xylosidase activity, or beta-glucosidase and beta-xylosidase activity depend on several factors including, but not limited to, the mixture of component cellulolytic and/or hemicellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having beta-glucosidase activity, beta-xylosidase activity, or beta-glucosidase and beta-xylosidase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having beta-glucosidase activity, beta-xylosidase activity, or beta-glucosidase and beta-xylosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli,*

*Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 2005/093050); *Thermobifida fusca* endoglucanase III (WO 2005/093050); and *Thermobifida fusca* endoglucanase V (WO 2005/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of further beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the methods of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 microM to about 1 M, e.g., about 0.5 microM to about 0.75 M, about 0.75 microM to about 0.5 M, about 1 microM to about 0.25 M, about 1 microM to about 0.1 M, about 5 microM to about 50 mM, about 10 microM to about 25 mM, about 50 microM to about 25 mM, about 10 microM to about 10 mM, about 5 microM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (UniProt accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (UniProt accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (Uni- Prot accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (UniProt accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (UniProt accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is

*Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another more preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, The biotechnological production of sorbitol, *Appl. MicrobioL Biotechnol*. 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka et al., 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy* 13(1-2): 83-114.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 22 of SEQ ID NO: 2, amino acids 1 to 22 of SEQ ID NO: 4, amino acids 1 to 19 of SEQ ID NO: 6, or amino acids 1 to 19 of SEQ ID NO: 8. The polynucleotides may further comprise a gene encoding a protein, which is operably linked to the signal peptide. The protein is preferably foreign to the signal peptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

Examples

Materials
Chemicals used as buffers and substrates were commercial products of at least reagent grade.
Strains
*Talaromyces leycettanus* strain CBS398.68, was used as the source of polypeptides having beta-glucosidase activity, beta-xylosidase activity, or beta-glucosidase and beta-xylosidase activity.

*Aspergillus oryzae* MT3568 strain was used for heterologous expression of the family GH3 gene encoding polypeptides having homology with polypeptides with beta-glucosidase or beta-xylosidase or beta-glucosidase and betaglucosidase activity. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.
Media and Solutions
YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 microliters/500 ml) was added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1: Genomic DNA Extraction

To generate genomic DNA for PCR amplification, the fungal strain was propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material from the above cultures were harvested by centrifugation at 14,000×g for 2 minutes. The supernatant was removed and the pellet resuspended in 500 microliters of deionized water. The suspension was transferred to a Lysing Matrix E FastPrep® tube (Qbiogene, Inc., Carlsbad, Calif., USA) and 790 microliters of sodium phosphate buffer and 100 microliters of MT buffer from the FastDNA® SPIN Kit were added to the tube. The sample was then secured in the FastPrep® Instrument (Qbiogene, Inc., Carlsbad, Calif., USA) and processed for 60 seconds at a speed of 5.5 m/sec. The sample was then centrifuged at 14000×g for two minutes and the supernatant transferred to a clean EPPENDORF® tube. A 250 microliter volume of PPS reagent from the FastDNA® SPIN Kit was added and then the sample was mixed gently by inversion. The sample was again centrifuged at 14000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 microliter volume of the supernatant was removed and discarded and then the remaining sample was resuspended in the matrix. The sample was then transferred to a SPIN filter tube from the FastDNA® SPIN Kit and centrifuged at 14000×g for 1 minute. The catch tube was emptied and the remaining matrix suspension added to the SPIN filter tube. The sample was again centrifuged (14000×g, 1 minute). A 500 microliter volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 microliters of DES (DNase/Pyrogen free water) with a pipette tip. The unit was centrifuged (14000×g, 1 minute) to elute the genomic DNA followed by elution with 100 microliters of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

Example 2: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, geneID (Parra et al., 2000, *Genome Research* 10(4): 511-515) was used for gene prediction. Blastall version 2.2.21 (National Center for Biotechnology Information (NCBI), Bethesda, Md., USA) and HMMER version 2.3.2 (sanger.ac.uk/resources/software/) were used to predict function based on structural homology. The family GH3 enzyme candidates were identified directly by analysis of the Blast results. Agene (Munch and Krogh, 2006, *BMC Bioinformatics* 7: 263) and SignalP (Nielsen et al., 1997, *Protein Engineering* 10: 1-6) were used to identify start codons.

Example 3: Construction of an *Aspergillus oryzae* Expression Vector Containing Genomic Sequences Encoding a Family GH3 Polypeptide Having Beta-Glucosidase Activity, Beta-Xylosidase Activity, or Beta-Glucosidase and Beta-Xylosidase Activity Synthetic oligonucleotide primers shown below (SEQ ID NO: 9 to SEQ ID NO: 16) were designed to PCR amplify GH3 genes from the genomic DNA prepared in Example 1. An IN-FUSION™ Cloning Kit (Clontech, Mountain View, Calif., USA) was used to clone the fragments directly into the expression vector pDau109 (WO 2005/042735).

```
Primer GH3_118f:
                                         (SEQ ID NO: 9)
ACACAACTGGGGATCCACCATGGCGTTCAAATCCGGCTATATGACGTGG Primer GH3_118r:
                                        (SEQ ID NO: 10)
AGATCTCGAGAAGCTTATTACCTTCCACCTTGAACACCAGAGAAGCTATA
GC Primer GH3_220f:
                                        (SEQ ID NO: 11)
ACACAACTGGGGATCCACCATGGCTCGACTATCATATCTCATGTCGTTCG
TTTTCTGT Primer GH3_220r:
                                        (SEQ ID NO: 12)
AGATCTCGAGAAGCTTACTACACGGCAAGGCATTGTGCTCCAACC Primer GH3_222f:
                                        (SEQ ID NO: 13)
ACACAACTGGGGATCCACCATGAGGCTTGGGTGGCTTGAGGTGG Primer GH3_222r:
                                        (SEQ ID NO: 14)
AGATCTCGAGAAGCTTATCAGTTGACCTGAGGCAATGTCGCCTGC Primer GH3_225f:
                                        (SEQ ID NO: 15)
ACACAACTGGGGATCCACCATGCTTGCTGAGCAAATCTTCCTGAGTGTTC
TG Primer GH3_225r:
                                        (SEQ ID NO: 16)
AGATCTCGAGAAGCTTATCAAATACGGAAAGATCCCTGCTCCCTAATGTC
CC
```

PCR reactions were carried out with genomic DNA prepared from Example 1 for amplification of the genes identified in Example 2. The PCR reaction was composed of 1 microliter of genomic DNA, 1 microliter of primer forward (f) (50 microM); 1 microliter of primer reverse (r) (50 microM); 10 microliters of 5×HF buffer (Finnzymes Oy, Finland), 2 microliters of 10 mM dNTP; 1 microliter of PHUSION® DNA polymerase (Finnzymes Oy, Finland), and PCR-grade water up to 50 microliters. Primer GH3-118f and GH3-118r were used simultaneously to PCR amplified SEQ ID NO: 1; Primer GH3-220f and GH3-220r were used simultaneously to PCR amplified SEQ ID NO: 3; Primer GH3-222f and GH3-222r were used simultaneously to PCR amplified SEQ ID NO: 5; Primer GH3-225f and GH3-225r were used simultaneously to PCR amplified SEQ ID NO: 7. The PCR reactions were performed using a DYAD PCR machine (Bio-Rad Laboratories, Inc., Hercules, Calif., USA) programmed for 2 minutes at 98° C. followed by 20 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products were isolated by 1.0% agarose gel electrophoresis using 40 mM Tris base, 20 mM sodium acetate, 1 mM disodium EDTA (TAE) buffer where approximately 2.4 to 3.1 kb PCR product bands were excised from the gels and purified using a GFX® PCR DNA and Gel Band Purification Kit (GE Healthcare, United Kingdom) according to manufacturer's instructions. DNA corresponding to the GH3 genes were cloned into the expression vector pDAu109 (WO 2005/042735) linearized with Bam HI and Hind III, using an IN-FUSION™ Dry-Down PCR Cloning Kit (BD Biosciences, Palo Alto, Calif., USA) according to the manufacturer's instructions.

A 2.5 microliter volume of the five times diluted ligation mixture was used to transform *E. coli* TOP10 chemically competent cells (Invitrogen, Carlsbad, Calif., USA). Five colonies were selected on LB agar plates containing 100 micrograms of ampicillin per ml and cultivated overnight in 3 ml of LB medium supplemented with 100 micrograms of ampicillin per ml. Plasmid DNA was purified using an E.Z.N.A.® Plasmid Mini Kit (Omega Bio-Tek, Inc., Norcross, Ga., USA) according to the manufacturer's instructions. The GH3 gene sequences were verified by Sanger sequencing with an Applied Biosystems Model 3730XL Automated DNA Sequencer using version 3.1 BIG-DYE™ terminator chemistry (Applied Biosystems, Inc., Foster City, Calif., USA). Nucleotide sequence data were scrutinized for quality and all sequences were compared to each other with assistance of PHRED/PHRAP software (University of Washington, Seattle, Wash., USA).

For each gene, one construct was selected (IF282#6, IF283#7, IF285#8, and IF286#7 for GH3_118, GH3_220, GH3_222, and GH3_225 respectively) for *Aspergillus* transformation as described in example 5.

Example 4: Characterization of the Genomic Sequences Encoding GH3 Polypeptides Having Beta-Glucosidase Activity, Beta-Xylosidase Activity, or Beta-Glucosidase and Beta-Xylosidase Activity The nucleotide sequence and deduced amino acid sequence of the *Talaromyces leycettanus* GH3 gene are shown in SEQ ID NO: 1 and SEQ ID NO: 2, respectively. The coding sequence is 3025 bp including the stop codon and is interrupted by three introns of 68 bp (nucleotides 282 to 349), 55 bp (nucleotides 461 to 515), and 49 bp (nucleotides 793 to 841). The encoded predicted protein is 950 amino acids. Using the SignalP program v.3 (Nielsen et al., 1997, *Protein Engineering* 10: 1-6), a signal peptide of 22 residues was predicted. The predicted mature protein contains 928 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Talaromyces leycettanus* gene encoding the GH3 polypeptide having beta-glucosidase activity, beta-xylosidase activity, or beta-glucosidase and beta-xylosidase activity shares 59.16% identity (excluding gaps) to the deduced maturated amino acid sequence of a GH3 family protein from *Talaromyces stipitatus* (SwissProt accession number B8MNC6).

The nucleotide sequence and deduced amino acid sequence of the *Talaromyces leycettanus* GH3 gene are shown in SEQ ID NO: 3 and SEQ ID NO: 4, respectively. The coding sequence is 2850 bp including the stop codon and is interrupted by four introns of 60 bp (nucleotides 226 to 285), 61 bp (nucleotides 515 to 575), 53 bp (nucleotides 899 to 951), and 69 bp (nucleotides 1204 to 1272). The encoded predicted protein is 868 amino acids. Using the SignalP program v.3 (Nielsen et al., 1997, *Protein Engineering* 10: 1-6), a signal peptide of 22 residues was predicted. The predicted mature protein contains 846 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Talaromyces leycettanus* gene encoding the maturated GH3 polypeptide having beta-glucosidase activity, beta-xylosidase activity, or beta-glucosidase and beta-xylosidase activity shares 82.58% identity (excluding gaps) to the deduced maturated amino acid sequence of a GH3 family protein from *Thermoascus aurantiacus* (SwissProt accession number Q4U4W7).

The nucleotide sequence and deduced amino acid sequence of the *Talaromyces leycettanus* GH3 gene are shown in SEQ ID NO: 5 and SEQ ID NO: 6, respectively. The coding sequence is 3041 bp including the stop codon and is interrupted by five introns of 170 bp (nucleotides 61 to 230), 77 bp (nucleotides 371 to 447), 62 bp (nucleotides 546 to 607), 85 bp (nucleotides 1800 to 1884), and 64 bp (nucleotides 2744 to 2807). The encoded predicted protein is 860 amino acids. Using the SignalP program v.3 (Nielsen et al., 1997, *Protein Engineering* 10: 1-6), a signal peptide of 19 residues was predicted. The predicted mature protein contains 841 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced maturated amino acid sequence of the *Talaromyces leycettanus* gene encoding the GH3 polypeptide having beta-glucosidase activity, beta-xylosidase activity, or beta-glucosidase and beta-xylosidase activity shares 78.55% identity (excluding gaps) to the deduced maturated amino acid sequence of a GH3 family protein from *Thermoascus aurantiacus* var. *levisporus* (SwissProt accession number A9UFC6).

The nucleotide sequence and deduced amino acid sequence of the *Talaromyces leycettanus* GH3 gene are shown in SEQ ID NO: 7 and SEQ ID NO: 8, respectively. The coding sequence is 2465 bp including the stop codon and is interrupted by four introns of 67 bp (nucleotides 529 to 595), 56 bp (nucleotides 1313 to 1368), 58 bp (nucleotides 1524 to 1581), and 70 bp (nucleotides 1989 to 2058). The encoded predicted protein is 737 amino acids. Using the SignalP program v.3 (Nielsen et al., 1997, supra), a signal peptide of 19 residues was predicted. The predicted mature protein contains 718 amino acids. A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the maturated deduced amino acid sequence of the *Thermoascus leycettanus* gene encoding the GH3 polypeptide having beta-glucosidase activity, beta-xylosidase activity, or beta-glucosidase and beta-xylosidase activity shares 82.87% identity (excluding gaps) to the maturated deduced amino acid sequence of a GH3 family protein from *Neosartorya fischeri* (SwissProt accession number A1DCV5).

Example 5: Transformation of *Aspergillus oryzae* with Genes Encoding Beta-Glucosidase or/and a Beta-Xylosidase from *Talaromyces leycettanus* and Selection of the Best Transformants Protoplasts of *Aspergillus oryzae* MT3568 (see strains chapter) were prepared according to WO 95/02043. One hundred microliters of protoplasts were mixed with 2.5-15 micrograms of the *Aspergillus* expression vector of either IF282#6, or IF283#7, or IF285#8, or IF286#7 (Example 3) and 250 microliters of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of sixteen transformants were inoculated into 0.5 ml of DAP-4C-1 medium supplemented with lactic acid and with diammonium phosphate in 96 deep well plates. After 4 days cultivation at 30° C., the culture broths were analyzed by SDS-PAGE using Novex® 4-20% Tris-Glycine Gel (Invitrogen Corporation, Carlsbad, Calif., USA) to identify the transformants producing the largest amount of recombinant beta-glucosidase or beta-xyloaisdase from *Talaromyces leycettanus*.

A colorimetric assay was carried out simultaneously to confirm the beta-glucosidase or beta xylosidase activity from our best transformants using 4-nitrophenyl-β-D-glucopyranoside (Sigma Aldrich N-7006) or 4-nitrophenyl-β-D-xylopyranoside (Sigma Aldrich N-2132) as substrate. The assays were carried out by preparing two stock solutions of 4-nitrophenyl-β-D-glucopyranoside and 4-nitrophenyl-β-D-xylopyranoside of 100 mM (using 0.4% dimethyl sulfoxide to pre-solubilize the chromogenic substrates) and incubating 10 microliters of each culture broth corresponding to the different transformants to the following mix: 10 microliters of 0.1% Tween, 10 microliters of buffer sodium citrate pH 6.0 1 M, 4 microliters of the substrate stock solution in a final volume of 100 microliters. Incubations were carried out for 30 minutes at 37° C. before reading absorbance at 405 nm. 100 microliters of 1 M sodium carbonate buffer pH 10.0 was added to each reaction and the absorbance re-analyzed at 405 nm.

For each series of transformants, the best expressors of beta-glucosidase or beta-xylosidase from *Talaromyces leycettanus* were selected based on the highest absorbance value at 405 nm (both before and after pH shift) corresponding to the best beta-glucosidase or beta-xylosidase activities and also based on the band intensity of the SDS-Page gel.

SEQ ID NO: 2 showed beta-xylosidase activity and SEQ ID NOS: 4 and 8 showed beta-glucosidase activity.

Spores of the best transformants were spread on COVE-Sucrose-T plates containing 0.01% TRITON® X-100 in order to isolate single colonies. The spreading was repeated twice in total on COVE-Sucrose-T plates, and then a single colony was spread on a COVE-N-Agar tube until sporulation.

Example 6: Fermentation of *Aspergillus oryzae* Transformed with the Gene Encoding an Endoglucanase from *Neurospora tetrasperma*

150 ml of DAP-4C-1 media supplemented with 5 ml of 20% lactic acid and 3.5 ml of 50% diammonium phosphate and spores from the best transformants were cultivated in shake flasks during 4 days at a temperature of 30° C. under 100 rpm agitation. Culture broths were harvested by filtration using a 0.2 micro-m filter device.

Example 7: Purification

SEQ ID NO: 2 (P23YZ9)
Filtrated broth was adjusted to pH 7.0 and filtrated on 0.22 micro-m PES filter (Nalge Nunc International, Nalgene labware cat#595-4520). Following, the filtrate was added 1.8 M ammonium sulphate. The filtrate was loaded onto a Phenyl Sepharose™ 6 Fast Flow column (high sub) (GE Healthcare, Piscataway, N.J., USA) equilibrated with 1.8 M ammonium sulphate, 25 mM HEPES pH7.0. After wash with 1.0 M ammonium sulphate, the bound proteins were batch eluted with 25 mM HEPES pH 7.0. Fractions were collected and analyzed by SDS-PAGE. The fractions were pooled and applied to a Sephadex™ G-25 (medium) (GE Healthcare, Piscataway, N.J., USA) column equilibrated in 25 mM HEPES pH 7.0. The pH was adjusted to pH7.5 and the fractions were applied to a SOURCE™ 15Q (GE Healthcare, Piscataway, N.J., USA) column equilibrated in 12.5 mM HEPES pH 7.5 and bound proteins were eluted with a linear gradient from 0-500 mM sodium chloride over 10CV. Fractions were collected and analyzed by SDS-PAGE.

SEQ ID NO: 4 (P23YZ7)
Filtrated broth was adjusted to pH 7.0 and filtrated on 0.22 micro-m PES filter (Nalge Nunc International, Nalgene labware cat#595-4520). Following, the filtrate was added 1.8 M ammonium sulphate. The filtrate was loaded onto a Phenyl Sepharose™ 6 Fast Flow column (high sub) (GE Healthcare, Piscataway, N.J., USA) equilibrated with 1.8 M ammonium sulphate, 25 mM HEPES pH7.0. After wash with 1.0 M ammonium sulphate, the bound proteins were batch eluted with 25 mM HEPES pH 7.0. Fractions were collected and analyzed by SDS-PAGE. The fractions were pooled and applied to a Sephadex™ G-25 (medium) (GE Healthcare, Piscataway, N.J., USA) column equilibrated in 25 mM HEPES pH 7.0. The fractions were applied to a SOURCE™ 15Q (GE Healthcare, Piscataway, N.J., USA) column equilibrated in 25 mM HEPES pH 7.0 and bound proteins were eluted with a linear gradient from 0-500 mM sodium chloride over 10CV. Fractions were collected and analyzed by SDS-PAGE.

SEQ ID NO: 8 (P23Z1V)
Filtrated broth was adjusted to pH 7.0 and filtrated on 0.22 micro-m PES filter (Nalge Nunc International, Nalgene labware cat#595-4520). Following, the filtrate was added 1.8 M ammonium sulphate. The filtrate was loaded onto a Phenyl Sepharose™ 6 Fast Flow column (high sub) (GE Healthcare, Piscataway, N.J., USA) equilibrated with 1.8 M ammonium sulphate, 25 mM HEPES pH7.0. After wash with 1.0 M ammonium sulphate, the bound proteins were batch eluted with 25 mM HEPES pH 7.0. Fractions were collected and analyzed by SDS-PAGE. The fractions were pooled and applied to a Sephadex™ G-25 (medium) (GE Healthcare, Piscataway, N.J., USA) column equilibrated in 25 mM HEPES pH 7.0. The fractions were applied to a SOURCE™ 15Q (GE Healthcare, Piscataway, N.J., USA) column equilibrated in 25 mM HEPES pH 7.0 and bound proteins were eluted with a linear gradient from 0-500 mM sodium chloride over 10CV. Fractions were collected and analyzed by SDS-PAGE.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A nucleic acid construct comprising an isolated polynucleotide encoding a polypeptide having beta-glucosidase activity, beta-xylosidase activity, or beta-glucosidase and beta-xylosidase activity, wherein the polynucleotide is operably linked to one or more heterologous control sequences that direct the production of the polypeptide in a recombinant host cell, and wherein the polypeptide having beta-glucosidase activity, beta-xylosidase activity, or beta-glucosidase and beta-xylosidase activity, is selected from the group consisting of:
  (a) a polypeptide having at least 90% sequence identity to amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8;
  (b) a polypeptide comprising amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8; and
  (c) a fragment of the polypeptide of amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8, wherein the fragment has beta-glucosidase activity, beta-xylosidase activity, or beta-glucosidase and beta-xylosidase activity.

2. A recombinant host cell transformed with the nucleic acid construct of claim 1.

3. A method of producing a polypeptide having beta-glucosidase activity, beta-xylosidase activity, or beta-glucosidase and beta-xylosidase activity, comprising:
  (a) cultivating the recombinant host cell of claim 2 under conditions conducive for production of the polypeptide; and
  (b) recovering the polypeptide.

4. A transgenic plant, plant part or plant cell transformed with the nucleic acid construct of claim 1.

5. A method of producing a polypeptide having beta-glucosidase activity, beta-xylosidase activity, or beta-glucosidase and beta-xylosidase activity, comprising:
  (a) cultivating the transgenic plant or plant cell of claim 4 under conditions conducive for production of the polypeptide; and
  (b) recovering the polypeptide.

6. A process of fermenting a cellulosic material or xylan-containing material, comprising: fermenting the cellulosic material or xylan-containing material with one or more fermenting microorganisms, wherein the cellulosic material or xylan-containing material is saccharified with an enzyme composition comprising a polypeptide having beta-glucosidase activity, beta-xylosidase activity, or beta-glucosidase and beta-xylosidase activity, wherein the polypeptide is selected from the group consisting of:
  (a) a polypeptide having at least 90% sequence identity to amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8;
  (b) a polypeptide comprising amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8; and
  (c) a fragment of the polypeptide of amino acids 23 to 950 of SEQ ID NO: 2, amino acids 23 to 868 of SEQ ID NO: 4, amino acids 20 to 860 of SEQ ID NO: 6, or amino acids 20 to 737 of SEQ ID NO: 8, wherein the fragment has beta-glucosidase activity, beta-xylosidase activity, or beta-glucosidase and beta-xylosidase activity.

7. The process of claim 6, wherein the fermenting of the cellulosic material or xylan-containing material produces a fermentation product.

8. The process of claim 7, further comprising recovering the fermentation product from the fermentation.

9. The method of claim 3, wherein the polypeptide has at least 90% sequence identity to amino acids 23 to 950 of SEQ ID NO: 2.

10. The method of claim 3, wherein the polypeptide has at least 95% sequence identity to amino acids 23 to 950 of SEQ ID NO: 2.

11. The method of claim 3, wherein the polypeptide has at least 97% sequence identity to amino acids 23 to 950 of SEQ ID NO: 2.

12. The method of claim 3, wherein the polypeptide comprises amino acids 23 to 950 of SEQ ID NO: 2.

13. The method of claim 3, wherein the polypeptide has at least 90% sequence identity to amino acids 23 to 868 of SEQ ID NO: 4.

14. The method of claim 3, wherein the polypeptide has at least 95% sequence identity to amino acids 23 to 868 of SEQ ID NO: 4.

15. The method of claim 3, wherein the polypeptide has at least 97% sequence identity to amino acids 23 to 868 of SEQ ID NO: 4.

16. The method of claim 3, wherein the polypeptide comprises amino acids 23 to 868 of SEQ ID NO: 4.

17. The method of claim 3, wherein the polypeptide has at least 90% sequence identity to amino acids 20 to 860 of SEQ ID NO: 6.

18. The method of claim 3, wherein the polypeptide has at least 95% sequence identity to amino acids 20 to 860 of SEQ ID NO: 6.

19. The method of claim 3, wherein the polypeptide has at least 97% sequence identity to amino acids 20 to 860 of SEQ ID NO: 6.

20. The method of claim 3, wherein the polypeptide comprises amino acids 20 to 860 of SEQ ID NO: 6.

21. The method of claim 3, wherein the polypeptide has at least 90% sequence identity to amino acids 20 to 737 of SEQ ID NO: 8.

22. The method of claim 3, wherein the polypeptide has at least 95% sequence identity to amino acids 20 to 737 of SEQ ID NO: 8.

23. The method of claim 3, wherein the polypeptide has at least 97% sequence identity to amino acids 20 to 737 of SEQ ID NO: 8.

24. The method of claim 3, wherein the polypeptide comprises amino acids 20 to 737 of SEQ ID NO: 8.

25. The process of claim 6, wherein the cellulosic material or xylan-containing material is pretreated.

26. The process of claim 6, wherein the enzyme composition further comprises one or more enzymes selected from the group consisting of a cellulase, a GH61 polypeptide, a hemicellulase, an esterase, an expansin, a laccase, a ligninolytic enzyme, a pectinase, a peroxidase, a protease, and a swollenin.

27. The process of claim 7, wherein the fermentation product is an alcohol, an alkane, an alkene, an amino acid, a cycloalkane, a gas, isoprene, a ketone, an organic acid, or polyketide.

* * * * *

SEQUENCE LISTING

<160> NUMBER OF SEQ ID NOS: 16

<210> SEQ ID NO 1
<211> LENGTH: 3025
<212> TYPE: DNA
<213> ORGANISM: Talaromyces leycettanus

<400> SEQUENCE: 1

```
atggcgttca aatccggcta tatgacgtgg ggtttgactc tacttgcagc ctcccatact      60
gttgcatctc ctctgtctcg accatcacag cggacttgtc ttcctcctat cagtcaaagc     120
tatactgcag atatttcctt cctgggttgt tatacggatg cagagactcg cgtcctttca     180
ggtggcgagg ccactgccct cccacagggt acaacacccc agtcatgtgc tgatgcttgt     240
ggtcttgctg gcttctccta cgctggagta gaatattcca ggttcgtggc tctacatcct     300
ctttttgatg tcacggatgt atgcttacat tacgttatga tcatatcagt caatgctact     360
gtggaaatac gatcggcagc ggtgctgtaa aacagcctga cagcacatgc acttatcagt     420
gcagtggtaa ttctactgaa atctgtggag gtacatggct gtatgtggaa tcctgtttat     480
atgtatattc catcttgctt accagatcct ctcagaattg acatttacca aatctcaaac     540
ccatcctcca atccaatccc tctgaatgcg aatgcgctgc ctgactgcac gcgggatccc     600
ctgtgtagca accctatttg cgacacgtct ctgagtcctg aagaacgtgt caagggtctt     660
atcagcaatt ttaccctgca ggaaaaggcc agcaatttga tgaactcgtc cccaggtgtc     720
caacggctgg gcctggtacc gtatcagtgg tggtcagagg gattacatgg tgttgccaac     780
tctcctggtg ttgtatgtgc ctgaatattc tactggggaa gtgggttttg ctaaccaagc     840
catgtttgtc caggtattta gctcgcccct gggctcaaac tggagttatg caaccagttt     900
cccaacgcca attctcatgg gagccgcctt tgacgatgac ttgattaaca aagtcgccca     960
ggtcatcggt aaagaggctc gcgcctttgg aaataatggc aaggcaggat tcgacttctg    1020
gactcccaat atcaacccct ttagagatcc tcgatggggc cgtggcctgg agaccccgg    1080
agaagatcca ttccatctca gaaattacgt ctataacctt atcacgggcc ttcagggagg    1140
cgtcgacccc gatgttcccc agatcattgc cacctgcaag cactttgcgg tctatgatgt    1200
tgaacatggt cgtgactcaa atgacctgaa ccctacgccc caagacctta ccgactactt    1260
tctgcctccc ttcaagacgt gcgccagaga cgcaaaggtt ggtgccgtca tgtgctctta    1320
caatgctgtc gacggcatcc cgagctgtgc caaccgctac ctgcttgaga ccatgcttcg    1380
tgaacactgg gagtggaatc aaccatatca ctgggtcaca tcggactgcg gggccgtcac    1440
tgatattgtc gatgcacacc attatgtcaa cagtgatgcc aatgctgcag ctgtggcgat    1500
taatgcagga actgatctgg gttgtgaagg aagcattgag aacaaccttg ttcaggccgt    1560
ggctgccaat gtgacgagag aggcaaccct agatcaatca ctcttccggc tttacttgtc    1620
tttgttgcgc ctgggctact ttgatccttc caataaaat gcttcgcttg gctgggccga    1680
cgtgggaaca cccgaggccc aaaacctggc atacgaagcc gctgttgagg gtatgacact    1740
gctgaagaac aatggcgttt tgcctttgcg caacgatgct tccaaggtag ctgtgatcgg    1800
tccatgggcg aacgccacag agcagatgca gggaaattac tacggcacgg ctccgtactt    1860
gatcagcccc ttgatggcca tgcaggccaa atggaagaac gtcgaatatg cttatggcgc    1920
```

```
ggatattaac agcacgaaca ctggcggctt tgccgatgca ttgtcgattg catcttctgc    1980
tgagacgatc atttactgtg gtggcattga cacttccatc gaggctgagg gtcttgacag    2040
acagagcatc gtctggcctg ccgctcaact tgacctgatc tcccagctgg cagcgctcaa    2100
gaagcccttg gtcgtcgtgc aattcggcgg tggccagctt gacgcaccg cgctgctcaa     2160 caacgacaac atcgacgcga ttgtctgggc aggttacccg ggacagtccg gaggagatgc    2220
ccttcgagat gttctcgatg gcaccaaatc tatcgctgga cgcctcccta tcactcaata    2280
cccggccgac tacgttgaca aggtgaacat tctcgatccc aacctgcgtc caacaccac     2340 caccggaaat cctggtagaa cttacaagtg gtactcgtcc ccagtcctcc ccttcggtta    2400
cggtctccac tacactaatt tcagcgcctc gtgggcgtca accccgggaa aggttcattc    2460
tatccctgga ctagtccagc cccaggatcc tcacgatgct cccggagcag tggagaatgc    2520 acccttt gcg acattcaaga tcaacgtgaa gaataccggc ggccccgcga agatggcttc    2580
ggactatgtt ggcatgctct tcctctcttc ggagaacgcc ggcccagcgc tcgtcctt     2640 gaagtctctg ccgggtatg gcgcttgtc taatgttaga gttggcgaaa cccaggcgct     2700
ctccgtcacc gtaccaattg gagcactggc tcgtgctgat gccaatggca acctcgtcat    2760
ctaccccggt gactacacca tttcgctcga cgttgactcc aagatttcct tcgagttcag    2820
cctcgtcggc cctgaaaccg tgatcgagcc tgttcctctt ccgccgatgt cgcctgttcc    2880
gatatcttac ctcggttgct acaagagcca gcgagcccta aacggccga ctgtcaactt     2940 gaagacttcg aacactcctc aggcctgtgc tgatcaatgt cacgcatctg gctatagctt    3000
ctctggtgtt caaggtggaa ggtaa                                          3025

<210> SEQ ID NO 2
<211> LENGTH: 950
<212> TYPE: PRT
<213> ORGANISM: Talaromyces leycettanus

<400> SEQUENCE: 2

Met Ala Phe Lys Ser Gly Tyr Met Thr Trp Gly Leu Thr Leu Leu Ala
1               5                   10                  15

Ala Ser His Thr Val Ala Ser Pro Leu Ser Arg Pro Ser Gln Arg Thr
                20                  25                  30

Cys Leu Pro Pro Ile Ser Gln Ser Tyr Thr Ala Asp Ile Ser Phe Leu
            35                  40                  45

Gly Cys Tyr Thr Asp Ala Glu Thr Arg Val Leu Ser Gly Gly Glu Ala
        50                  55                  60

Thr Ala Leu Pro Gln Gly Thr Thr Pro Gln Ser Cys Ala Asp Ala Cys
65                  70                  75                  80

Gly Leu Ala Gly Phe Ser Tyr Ala Gly Val Glu Tyr Ser Ser Gln Cys
                85                  90                  95

Tyr Cys Gly Asn Thr Ile Gly Ser Gly Ala Val Lys Gln Pro Asp Ser
            100                 105                 110

Thr Cys Thr Tyr Gln Cys Ser Gly Asn Ser Thr Glu Ile Cys Gly Gly
        115                 120                 125

Thr Trp Leu Ile Asp Ile Tyr Gln Ile Ser Asn Pro Ser Ser Asn Pro
    130                 135                 140

Ile Pro Leu Asn Ala Asn Ala Leu Pro Asp Cys Thr Arg Asp Pro Leu
145                 150                 155                 160

Cys Ser Asn Pro Ile Cys Asp Thr Ser Leu Ser Pro Glu Glu Arg Val
                165                 170                 175
```

```
Lys Gly Leu Ile Ser Asn Phe Thr Leu Gln Glu Lys Ala Ser Asn Leu
            180                 185                 190

Met Asn Ser Ser Pro Gly Val Gln Arg Leu Gly Leu Val Pro Tyr Gln
        195                 200                 205

Trp Trp Ser Glu Gly Leu His Gly Val Ala Asn Ser Pro Gly Val Met
210                 215                 220

Phe Val Gln Val Phe Ser Ser Pro Leu Gly Ser Asn Trp Ser Tyr Ala
225                 230                 235                 240

Thr Ser Phe Pro Thr Pro Ile Leu Met Gly Ala Ala Phe Asp Asp Asp
                245                 250                 255

Leu Ile Asn Lys Val Ala Gln Val Ile Gly Lys Glu Ala Arg Ala Phe
            260                 265                 270

Gly Asn Asn Gly Lys Ala Gly Phe Asp Phe Trp Thr Pro Asn Ile Asn
        275                 280                 285

Pro Phe Arg Asp Pro Arg Trp Gly Arg Gly Leu Glu Thr Pro Gly Glu
    290                 295                 300

Asp Pro Phe His Leu Arg Asn Tyr Val Tyr Asn Leu Ile Thr Gly Leu
305                 310                 315                 320

Gln Gly Gly Val Asp Pro Asp Val Pro Gln Ile Ile Ala Thr Cys Lys
                325                 330                 335

His Phe Ala Val Tyr Asp Val Glu His Gly Arg Asp Ser Asn Asp Leu
            340                 345                 350

Asn Pro Thr Pro Gln Asp Leu Thr Asp Tyr Phe Leu Pro Pro Phe Lys
        355                 360                 365

Thr Cys Ala Arg Asp Ala Lys Val Gly Ala Val Met Cys Ser Tyr Asn
    370                 375                 380

Ala Val Asp Gly Ile Pro Ser Cys Ala Asn Arg Tyr Leu Leu Glu Thr
385                 390                 395                 400

Met Leu Arg Glu His Trp Glu Trp Asn Gln Pro Tyr His Trp Val Thr
                405                 410                 415

Ser Asp Cys Gly Ala Val Thr Asp Ile Val Asp Ala His His Tyr Val
            420                 425                 430

Asn Ser Asp Ala Asn Ala Ala Val Ala Ile Asn Ala Gly Thr Asp
        435                 440                 445

Leu Gly Cys Glu Gly Ser Ile Glu Asn Asn Leu Val Gln Ala Val Ala
    450                 455                 460

Ala Asn Val Thr Arg Glu Ala Thr Leu Asp Gln Ser Leu Phe Arg Leu
465                 470                 475                 480

Tyr Leu Ser Leu Leu Arg Leu Gly Tyr Phe Asp Pro Ser Asn Lys Tyr
                485                 490                 495

Ala Ser Leu Gly Trp Ala Asp Val Gly Thr Pro Glu Ala Gln Asn Leu
            500                 505                 510

Ala Tyr Glu Ala Ala Val Glu Gly Met Thr Leu Leu Lys Asn Asn Gly
        515                 520                 525

Val Leu Pro Leu Arg Asn Asp Ala Ser Lys Val Ala Val Ile Gly Pro
    530                 535                 540

Trp Ala Asn Ala Thr Glu Gln Met Gln Gly Asn Tyr Tyr Gly Thr Ala
545                 550                 555                 560

Pro Tyr Leu Ile Ser Pro Leu Met Ala Met Gln Ala Lys Trp Lys Asn
                565                 570                 575

Val Glu Tyr Ala Tyr Gly Ala Asp Ile Asn Ser Thr Asn Thr Gly Gly
            580                 585                 590
```

Phe Ala Asp Ala Leu Ser Ile Ala Ser Ser Ala Glu Thr Ile Ile Tyr
            595                 600                 605

Cys Gly Gly Ile Asp Thr Ser Ile Glu Ala Glu Gly Leu Asp Arg Gln
    610                 615                 620

Ser Ile Val Trp Pro Ala Ala Gln Leu Asp Leu Ile Ser Gln Leu Ala
625                 630                 635                 640

Ala Leu Lys Lys Pro Leu Val Val Gln Phe Gly Gly Gln Leu
                645                 650                 655

Asp Asp Thr Ala Leu Leu Asn Asn Asp Asn Ile Asp Ala Ile Val Trp
            660                 665                 670

Ala Gly Tyr Pro Gly Gln Ser Gly Asp Ala Leu Arg Asp Val Leu
            675                 680                 685

Asp Gly Thr Lys Ser Ile Ala Gly Arg Leu Pro Ile Thr Gln Tyr Pro
            690                 695                 700

Ala Asp Tyr Val Asp Lys Val Asn Ile Leu Asp Pro Asn Leu Arg Pro
705                 710                 715                 720

Asn Thr Thr Thr Gly Asn Pro Gly Arg Thr Tyr Lys Trp Tyr Ser Ser
                725                 730                 735

Pro Val Leu Pro Phe Gly Tyr Gly Leu His Tyr Thr Asn Phe Ser Ala
                740                 745                 750

Ser Trp Ala Ser Thr Pro Gly Lys Val His Ser Ile Pro Gly Leu Val
            755                 760                 765

Gln Pro Gln Asp Pro His Asp Ala Pro Gly Ala Val Glu Asn Ala Pro
            770                 775                 780

Phe Ala Thr Phe Lys Ile Asn Val Lys Asn Thr Gly Gly Pro Ala Lys
785                 790                 795                 800

Met Ala Ser Asp Tyr Val Gly Met Leu Phe Leu Ser Ser Glu Asn Ala
                805                 810                 815

Gly Pro Ala Pro Arg Pro Leu Lys Ser Leu Ala Gly Tyr Gly Arg Leu
            820                 825                 830

Ser Asn Val Arg Val Gly Glu Thr Gln Ala Leu Ser Val Thr Val Pro
            835                 840                 845

Ile Gly Ala Leu Ala Arg Ala Asp Ala Asn Gly Asn Leu Val Ile Tyr
850                 855                 860

Pro Gly Asp Tyr Thr Ile Ser Leu Asp Val Asp Ser Lys Ile Ser Phe
865                 870                 875                 880

Glu Phe Ser Leu Val Gly Pro Glu Thr Val Ile Glu Pro Val Pro Leu
                885                 890                 895

Pro Pro Met Ser Pro Val Pro Ile Ser Tyr Leu Gly Cys Tyr Lys Ser
            900                 905                 910

Gln Arg Ala Leu Asn Gly Pro Thr Val Asn Leu Lys Thr Ser Asn Thr
            915                 920                 925

Pro Gln Ala Cys Ala Asp Gln Cys His Ala Ser Gly Tyr Ser Phe Ser
            930                 935                 940

Gly Val Gln Gly Gly Arg
945                 950

<210> SEQ ID NO 3
<211> LENGTH: 2850
<212> TYPE: DNA
<213> ORGANISM: Talaromyces leycettanus

<400> SEQUENCE: 3
atggctcgac tatcatatct catgtcgttc gttttctgtg ctacgttggg atcctcctct       60

```
tccgcaggag acccagtagc tgagcgcggg cgtttgaaat ctcgggacac tacttacaca    120
tcggctcctt actatcctgc tccaaatggc ggatggatca gcgactgggc gtcggcctat    180
gagaaagctc atgcggttgt ttcgaacatg acgttagctg agaaggtctg tctaagctca    240
agtttcttcg agataaccgt cgtccgctga tgagaaatcc aataggtcaa cctgacaaca    300
ggcactggat tctacatggg gccatgcgta ggacagactg gaagtgccct ccggtttgga    360
atccccaatc tgtgccttca agactcgccg ctgggtatcc gcaatacaga tcacaacact    420
gcgttcccgg ctggtatcac cgtcggagcg acgttcgata aagaccttat gtatgcgcgt    480
ggaaaagccc tgggcgagga ggcgcgcggc aagggtatat gaatcaccta tccgaatact    540
ccaaaggata ttccacgact aacctaattg cacaggagta aatgtacagc tgggtccatg    600
cgtagggcca ttaggtcgta aaccccgagg tgggcgcaac tgggagggct tcggtgcgga    660
ccccagtctt caggcaattg cagcagcgca gacgatcaag ggcatgcaaa gtaccggcgt    720
gattgcgacg atcaagcact ttatcggcta tgagcaggaa atgtaccgga tgacgaacgt    780
gctccagaag ggatactctt ccaatattga tgacaggacg ctacatgagc tctatctgtg    840
gccattcgca gaaggtgtca gagccggggt aggctctgtg atgatggcat acaatgatgt    900
aggccattgg aagatggccc caatgttcat cctttgctga ctgcttttta ggtgaacggt    960
tcgacgtgca gtcaaaatag cagactgatc aacggcatcc tcaaggacga actcggattc   1020
cagggctttg tagtgacaga ttggctaggg caaataggcg gtgtctcgtc agcattagca   1080
ggtctggaca tgagtatgcc cggtgatggt gtaattccac tgcttggaga cagctactgg   1140
gcgtacgagt tgtcccgcgc ggtcctcaac ggaactgttc ccgtcgagcg cctgaatgac   1200
atggtacgga ttattgaagc ttccctgctt gaaactccgt cgttcactgg catcttctga   1260
cgtgctgtcc aggtcactcg catcgtagca acctggtaca aactgggcca ggataaggac   1320
tatcctctgc caaatttctc gacgaacacg gaggatgcta ctggccctct gtaccccggg   1380
gcgcttttct cgcctactgg agttgtcaac cagtttgtca atgtgcaagg tgatcacaat   1440
atcactgcaa gagctgttgc cagggacgct atcacgcttc tcaagaacga caacaacacg   1500
ctaccattgt cgcgaaatga gtccttgaag gtcttcggga cagacgccgg accgaatcca   1560
gacggtctta attcctgcag cgaccgcggt tgcgacaaag gcgtgttgac tatgggctgg   1620
ggatctggga cttcaagact cccataccte atcacaccac aagaggctat ggcaacgcc    1680 ttctcgaatg cagaattcta tatcaccgac gatttcccac caggcattac agccaatgcc   1740
aacgacattg caattgtctt catcaacgcc gattccggtg agaactacat caccgtggaa   1800
ggcaaccccg gtgatcgaac ggtggcaggg ctttatgcat ggcataatgg ggacgagctc   1860
gtcaaagcag cggcagggaa gttctctacg gtcgtggtag ttgtccacac tgtcggtcct   1920
attctgatgg aagagtggat tgatctggag gccgtcaaag cggtcgtggt tgcgcatctg   1980
ccaggtcaag aagctggcga ctccttagtt gatgttctct tcggcgatta cagtcccagt   2040
ggtcatctac cctatacaat tccgcgcagt gaattggatt accegtcgag cgtgagcttg   2100 atagaccagc acttgggcca gatccaagac acttttttcgg agggtctgta catcgattat   2160
cgctacttgt tgaaaaccaa cgcgacgccg cgatatccat tcgggcacgg tttatcatac   2220
acgacgtttg aatactcaga ggcgacccta tccctcgtca ctccattaag cagcggatat   2280
cctccagctc gcccaacaaa aggcccaaca cctccatacg ccaccaccat ccctcccaca   2340
tctgaagtag cgtggcctgg ccacttcgac cgaatcggc gctatctata cccgtacctg   2400
gatgatcctg aagcggcaac ctcgacggct ccctatcctt atcccacagg ctacacgaca   2460
```

```
actccgcaac cagccccacg tgcaggaggg gcagaaggag gtaaccctgc tctttgggac    2520
gttgccttct cagtgacggt caaagtaacc aacaccggca gacggcccgg tcgtgccgtg    2580
gtgcaggtct acgtgcaact tccttccagc cttggtcttg acacgccgtc tttgcaattg    2640
cgacagtttg aaaagacccg cattttggca aagggagaaa gtgaggttct gacgatggag    2700
ataactcgga aagatctgag cgtgtgggat gttgtagtgc aggactggaa ggcacctgtc    2760
aatggggagg gggtcaagat ctacattggc gagagtgttg ctgatttgcg tctggtttgt    2820
gaggttggag cacaatgcct tgccgtgtag                                     2850
```

<210> SEQ ID NO 4
<211> LENGTH: 868
<212> TYPE: PRT
<213> ORGANISM: Talaromyces leycettanus

<400> SEQUENCE: 4

```
Met Ala Arg Leu Ser Tyr Leu Met Ser Phe Val Phe Cys Ala Thr Leu
1               5                   10                  15

Gly Ser Ser Ser Ala Gly Asp Pro Val Ala Glu Arg Gly Arg Leu
            20                  25                  30

Lys Ser Arg Asp Thr Thr Tyr Thr Ser Ala Pro Tyr Tyr Pro Ala Pro
        35                  40                  45

Asn Gly Gly Trp Ile Ser Asp Trp Ala Ser Ala Tyr Glu Lys Ala His
    50                  55                  60

Ala Val Val Ser Asn Met Thr Leu Ala Glu Lys Val Asn Leu Thr Thr
65                  70                  75                  80

Gly Thr Gly Phe Tyr Met Gly Pro Cys Val Gly Gln Thr Gly Ser Ala
                85                  90                  95

Leu Arg Phe Gly Ile Pro Asn Leu Cys Leu Gln Asp Ser Pro Leu Gly
            100                 105                 110

Ile Arg Asn Thr Asp His Asn Thr Ala Phe Pro Ala Gly Ile Thr Val
        115                 120                 125

Gly Ala Thr Phe Asp Lys Asp Leu Met Tyr Ala Arg Gly Lys Ala Leu
    130                 135                 140

Gly Glu Glu Ala Arg Gly Lys Gly Val Asn Val Gln Leu Gly Pro Cys
145                 150                 155                 160

Val Gly Pro Leu Gly Arg Lys Pro Arg Gly Gly Arg Asn Trp Glu Gly
                165                 170                 175

Phe Gly Ala Asp Pro Ser Leu Gln Ala Ile Ala Ala Gln Thr Ile
            180                 185                 190

Lys Gly Met Gln Ser Thr Gly Val Ile Ala Thr Ile Lys His Phe Ile
        195                 200                 205

Gly Tyr Glu Gln Glu Met Tyr Arg Met Thr Asn Val Leu Gln Lys Gly
    210                 215                 220

Tyr Ser Ser Asn Ile Asp Asp Arg Thr Leu His Glu Leu Tyr Leu Trp
225                 230                 235                 240

Pro Phe Ala Glu Gly Val Arg Ala Gly Val Gly Ser Val Met Met Ala
                245                 250                 255

Tyr Asn Asp Val Asn Gly Ser Thr Cys Ser Gln Asn Ser Arg Leu Ile
            260                 265                 270

Asn Gly Ile Leu Lys Asp Glu Leu Gly Phe Gln Gly Phe Val Val Thr
        275                 280                 285

Asp Trp Leu Gly Gln Ile Gly Gly Val Ser Ser Ala Leu Ala Gly Leu
    290                 295                 300
```

-continued

Asp Met Ser Met Pro Gly Asp Gly Val Ile Pro Leu Leu Gly Asp Ser
305                 310                 315                 320

Tyr Trp Ala Tyr Glu Leu Ser Arg Ala Val Leu Asn Gly Thr Val Pro
            325                 330                 335

Val Glu Arg Leu Asn Asp Met Val Thr Arg Ile Val Ala Thr Trp Tyr
        340                 345                 350

Lys Leu Gly Gln Asp Lys Asp Tyr Pro Leu Pro Asn Phe Ser Thr Asn
    355                 360                 365

Thr Glu Asp Ala Thr Gly Pro Leu Tyr Pro Gly Ala Leu Phe Ser Pro
370                 375                 380

Thr Gly Val Val Asn Gln Phe Val Asn Val Gln Gly Asp His Asn Ile
385                 390                 395                 400

Thr Ala Arg Ala Val Ala Arg Asp Ala Ile Thr Leu Leu Lys Asn Asp
                405                 410                 415

Asn Asn Thr Leu Pro Leu Ser Arg Asn Glu Ser Leu Lys Val Phe Gly
            420                 425                 430

Thr Asp Ala Gly Pro Asn Pro Asp Gly Leu Asn Ser Cys Ser Asp Arg
        435                 440                 445

Gly Cys Asp Lys Gly Val Leu Thr Met Gly Trp Gly Ser Gly Thr Ser
450                 455                 460

Arg Leu Pro Tyr Leu Ile Thr Pro Gln Glu Ala Ile Gly Asn Ala Phe
465                 470                 475                 480

Ser Asn Ala Glu Phe Tyr Ile Thr Asp Asp Phe Pro Pro Gly Ile Thr
                485                 490                 495

Ala Asn Ala Asn Asp Ile Ala Ile Val Phe Ile Asn Ala Asp Ser Gly
            500                 505                 510

Glu Asn Tyr Ile Thr Val Glu Gly Asn Pro Gly Asp Arg Thr Val Ala
        515                 520                 525

Gly Leu Tyr Ala Trp His Asn Gly Asp Glu Leu Val Lys Ala Ala Ala
    530                 535                 540

Gly Lys Phe Ser Thr Val Val Val Val His Thr Val Gly Pro Ile
545                 550                 555                 560

Leu Met Glu Glu Trp Ile Asp Leu Glu Ala Val Lys Ala Val Val Val
                565                 570                 575

Ala His Leu Pro Gly Gln Glu Ala Gly Asp Ser Leu Val Asp Val Leu
            580                 585                 590

Phe Gly Asp Tyr Ser Pro Ser Gly His Leu Pro Tyr Thr Ile Pro Arg
        595                 600                 605

Ser Glu Leu Asp Tyr Pro Ser Ser Val Ser Leu Ile Asp Gln His Leu
    610                 615                 620

Gly Gln Ile Gln Asp Thr Phe Ser Glu Gly Leu Tyr Ile Asp Tyr Arg
625                 630                 635                 640

Tyr Leu Leu Lys Thr Asn Ala Thr Pro Arg Tyr Pro Phe Gly His Gly
                645                 650                 655

Leu Ser Tyr Thr Thr Phe Glu Tyr Ser Glu Ala Thr Leu Ser Leu Val
            660                 665                 670

Thr Pro Leu Ser Ser Gly Tyr Pro Pro Ala Arg Pro Thr Lys Gly Pro
        675                 680                 685

Thr Pro Pro Tyr Ala Thr Thr Ile Pro Pro Thr Ser Glu Val Ala Trp
    690                 695                 700

Pro Gly His Phe Asp Arg Ile Trp Arg Tyr Leu Tyr Pro Tyr Leu Asp
705                 710                 715                 720

```
Asp Pro Glu Ala Ala Thr Ser Thr Ala Pro Tyr Pro Tyr Pro Thr Gly
                725                 730                 735

Tyr Thr Thr Thr Pro Gln Pro Ala Pro Arg Ala Gly Gly Ala Glu Gly
            740                 745                 750

Gly Asn Pro Ala Leu Trp Asp Val Ala Phe Ser Val Thr Val Lys Val
        755                 760                 765

Thr Asn Thr Gly Arg Arg Pro Gly Arg Ala Val Val Gln Val Tyr Val
    770                 775                 780

Gln Leu Pro Ser Ser Leu Gly Leu Asp Thr Pro Ser Leu Gln Leu Arg
785                 790                 795                 800

Gln Phe Glu Lys Thr Arg Ile Leu Ala Lys Gly Glu Ser Glu Val Leu
                805                 810                 815

Thr Met Glu Ile Thr Arg Lys Asp Leu Ser Val Trp Asp Val Val
            820                 825                 830

Gln Asp Trp Lys Ala Pro Val Asn Gly Glu Gly Val Lys Ile Tyr Ile
        835                 840                 845

Gly Glu Ser Val Ala Asp Leu Arg Leu Val Cys Glu Val Gly Ala Gln
    850                 855                 860

Cys Leu Ala Val
865

<210> SEQ ID NO 5
<211> LENGTH: 3041
<212> TYPE: DNA
<213> ORGANISM: Talaromyces leycettanus

<400> SEQUENCE: 5
atgaggcttg gtggcttga ggtggccgca cttgcggttg ccaccgttgc tgatgccaag      60
gtagctctcc ccgacaggct aattagtgct tctgacccca gcttgcctcg gatcactcta     120
attgaactgt catttctctc ttgttcatcg gaaatgcgac aaagcaacat atctggtcaa     180
ttgatggaac acttctaaga aaagtgacct gctaacccgg actgcatcag gacctggctt     240
attgtccccc attctacccg tcaccatggg cagacggcaa tggagagtgg gcggaggctc     300
acagtcgtgc cgtggaattt gtgtcaggcc tcacgcttgc tgagaaggtc aatctcacga     360
ctggtgttgg gtaggtcgac tgtgattcct ccatttccaa gggcaaaccg ttgttttcat     420
gagccatttt ttactgatat cacatagttg gatgggagaa acgtgtgtcg gtaataccgg     480
tagcattccc agactcggat tttggggatt ttgcgcccaa gattctcccc ttggtgttcg     540
agacagtaag gctcttcctt gagttgtctg ctttcttcac tgtcttttat tgacattcct     600
cctccagctg attacaattc cgctttcccc gcgggtgtca atgttgccgc tacctgggac     660
aagaaccttg cctacctccg gggtagagcc atgggtgaag aacaccgtga caaaggcgtg     720
gacgttcaac ttggcccagt cgctggtcct ctcggcagag cgcccgaagg tggcagaaac     780
tgggagggct tcggtcctga ccctgtcttg accggtcaat tgatggcgga gaccatcaag     840
ggtattcagg atgtcggtgt tattgcctgt gcaaagcatt ttatcctcaa cgagcaggag     900
cactttcgcc aggttgggga ggctcaaggc tatggctaca atattacgca agccattagc     960
tccaacattg acgacaagac ccttcacgaa ttgtacctgt ggccctttgc ggatgccgtg    1020
cgtgctggcg tgggctcggt gatgtgctct tacaaccaga tcaacaacag ttacggatgc    1080
tcgaacagct acacgatgaa caagctgctc aaaggtgaac tcaactttca gggcttcatc    1140
atgagcgact ggcaggcgca taaagtggt gttggcgacg ccttggctgg tctgacacatg    1200 tcgatgccgg gtgacactac cttcaacacc ggagagtcct actgggcac caacctgact    1260
```

```
attgccgtct tgaacggcac catccctgag tggcgtattg acgacatggc cgtccgcatc    1320
atgtcggctt tctacaaggt cggccgtgac cgtgtccgca ctcctccaaa cttcagctca    1380
tggaccaccg acgaatatgg ctacgagcat gctgctgtca accagggcta cgaaggtc     1440 aacgacagag ttgatgtgcg ctctaaccat aaagatatta ttcgccaggt tggctcttcc    1500
agcgtcgtcc ttttgaaaaa ccagtgggga gcacttccct tgactggcaa ggagaagctt    1560
gttggtatca tgggtgaaga cgcaggatcc aatgcttatg cgttaatgg ctgcagtgac     1620 cgcggctgcg acaacggcac tttggccatg ggctgggca gtggcaccgc aaacttccct     1680
tacctcatca ctcccgagca ggccatccaa tgggaagtca tcgagagcgg gggtgaggtc    1740
ttcgcgatca ccgacaacgg ggcccttgac cagatggcgt ctgttgcatc tcaggctagg    1800
taagctttca tatccctat tacgatctgc gagtggacgc ttgagttttg cggttgtagt     1860
ttcttcgcta atatagattc acagcgtgtc ccttgtgttc gtgaacgccg actctggaga    1920
aggttacatc aatgtcgatg gcaatgaggg agatcgtaag aacctcactc tctggaagaa    1980
cggagatgag gttatcaaga ctgtcgcggc caactgcaac aacaccattg tggtgatgca    2040
taccgtcgga cctgttcttg tcactgagtg gtacgcacaa cccaacatca ccgcaattct    2100
ctgggctggt cttcctggcg agcagagcgg caactctttg gtcgatgtgc tctacggccg    2160
tgtcaaccct ggcggcaaga ctccattcac ctggggcaag agtttcgact cgtgggggttc   2220 tcatgtaatg actacgccca caacggcaa tgatgcgcca cagctggatt ctcggaagg     2280 cgttttcatc gactacagat ggtttgacaa gaacaacgag actcccattt acgagttcgg    2340
ttacggtctg agctacacca cgttcaagta ctccaacctt caggtcacgc ccttgaatgc    2400
ccccaagtac accctgcta gtggaaagac cgaccctgct cccagtttcg acagcctgg     2460 cagcgcgtcc caatatgtgt tcccacgtac actgaacaga atctacgagt acatctaccc    2520
gtggttgaac tcgaccaacc tcagggagtc gtcgggagat cccgactatg catgaaggc    2580 gtctgcatac atcccggccg gcgcaacaga tggatctgcg caagagctgc ttccagccag    2640
cggtgctcct ggtggcaacc ctggtctta tgacgagctg ttcagggtct ctgctaccat    2700
cactaacacc ggcaaagtcg ctggtgatga ggttcccccaa ttggtaagct tccatgctac    2760
atacgccttc gttgtgagag tcttgacact aattccatgc tctacagtat gtctctcttg    2820
gcggtcctaa cgaccccaag gttgttctcc gcaacttcga ccgcatcaac attgctccgg    2880
gccagtccgt cgagtggact accactctga cccgacgtga cctctccaac tgggatgttg    2940
cggcccagga ctgggtcatt agcaagtacc ccaagacggt ctatgttggt agctcttctc    3000
gcaagcttcc tctgcaggcg acattgcctc aggtcaactg a                        3041
```

<210> SEQ ID NO 6
<211> LENGTH: 860
<212> TYPE: PRT
<213> ORGANISM: Talaromyces leycettanus

<400> SEQUENCE: 6

Met Arg Leu Gly Trp Leu Glu Val Ala Ala Leu Ala Val Ala Thr Val
1               5                   10                  15

Ala Asp Ala Lys Asp Leu Ala Tyr Cys Pro Pro Phe Tyr Pro Ser Pro
                20                  25                  30

Trp Ala Asp Gly Asn Gly Glu Trp Ala Glu Ala His Ser Arg Ala Val
            35                  40                  45

Glu Phe Val Ser Gly Leu Thr Leu Ala Glu Lys Val Asn Leu Thr Thr

-continued

```
                50                  55                  60
Gly Val Gly Trp Met Gly Glu Thr Cys Val Gly Asn Thr Gly Ser Ile
 65                  70                  75                  80

Pro Arg Leu Gly Phe Trp Gly Phe Cys Ala Gln Asp Ser Pro Leu Gly
                     85                  90                  95

Val Arg Asp Thr Asp Tyr Asn Ser Ala Phe Pro Ala Gly Val Asn Val
                100                 105                 110

Ala Ala Thr Trp Asp Lys Asn Leu Ala Tyr Leu Arg Gly Arg Ala Met
                115                 120                 125

Gly Glu Glu His Arg Asp Lys Gly Val Asp Val Gln Leu Gly Pro Val
            130                 135                 140

Ala Gly Pro Leu Gly Arg Ala Pro Glu Gly Gly Arg Asn Trp Glu Gly
145                 150                 155                 160

Phe Gly Pro Asp Pro Val Leu Thr Gly Gln Leu Met Ala Glu Thr Ile
                165                 170                 175

Lys Gly Ile Gln Asp Val Gly Val Ile Ala Cys Ala Lys His Phe Ile
                180                 185                 190

Leu Asn Glu Gln Glu His Phe Arg Gln Val Gly Glu Ala Gln Gly Tyr
            195                 200                 205

Gly Tyr Asn Ile Thr Gln Ala Ile Ser Ser Asn Ile Asp Asp Lys Thr
            210                 215                 220

Leu His Glu Leu Tyr Leu Trp Pro Phe Ala Asp Ala Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Met Asn Lys Leu Leu Lys Gly Glu Leu Asn
                260                 265                 270

Phe Gln Gly Phe Ile Met Ser Asp Trp Gln Ala His Lys Ser Gly Val
            275                 280                 285

Gly Asp Ala Leu Ala Gly Leu Asp Met Ser Met Pro Gly Asp Thr Thr
            290                 295                 300

Phe Asn Thr Gly Glu Ser Tyr Trp Gly Thr Asn Leu Thr Ile Ala Val
305                 310                 315                 320

Leu Asn Gly Thr Ile Pro Glu Trp Arg Ile Asp Asp Met Ala Val Arg
                325                 330                 335

Ile Met Ser Ala Phe Tyr Lys Val Gly Arg Asp Arg Val Arg Thr Pro
                340                 345                 350

Pro Asn Phe Ser Ser Trp Thr Thr Asp Glu Tyr Gly Tyr Glu His Ala
            355                 360                 365

Ala Val Asn Gln Gly Tyr Thr Lys Val Asn Asp Arg Val Asp Val Arg
            370                 375                 380

Ser Asn His Lys Asp Ile Ile Arg Gln Val Gly Ser Ser Ser Val Val
385                 390                 395                 400

Leu Leu Lys Asn Gln Trp Gly Ala Leu Pro Leu Thr Gly Lys Glu Lys
                405                 410                 415

Leu Val Gly Ile Met Gly Glu Asp Ala Gly Ser Asn Ala Tyr Gly Val
                420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Ile Thr Pro Glu Gln
            450                 455                 460

Ala Ile Gln Trp Glu Val Ile Glu Ser Gly Gly Glu Val Phe Ala Ile
465                 470                 475                 480
```

Thr Asp Asn Gly Ala Leu Asp Gln Met Ala Ser Val Ala Ser Gln Ala
                485                 490                 495

Ser Val Ser Leu Val Phe Val Asn Ala Asp Ser Gly Glu Gly Tyr Ile
            500                 505                 510

Asn Val Asp Gly Asn Glu Gly Asp Arg Lys Asn Leu Thr Leu Trp Lys
            515                 520                 525

Asn Gly Asp Glu Val Ile Lys Thr Val Ala Ala Asn Cys Asn Asn Thr
        530                 535                 540

Ile Val Val Met His Thr Val Gly Pro Val Leu Val Thr Glu Trp Tyr
545                 550                 555                 560

Asp Asn Pro Asn Ile Thr Ala Ile Leu Trp Ala Gly Leu Pro Gly Glu
                565                 570                 575

Gln Ser Gly Asn Ser Leu Val Asp Val Leu Tyr Gly Arg Val Asn Pro
            580                 585                 590

Gly Gly Lys Thr Pro Phe Thr Trp Gly Lys Ser Phe Asp Ser Trp Gly
            595                 600                 605

Ser His Val Met Thr Thr Pro Asn Asn Gly Asn Asp Ala Pro Gln Leu
        610                 615                 620

Asp Phe Ser Glu Gly Val Phe Ile Asp Tyr Arg Trp Phe Asp Lys Asn
625                 630                 635                 640

Asn Glu Thr Pro Ile Tyr Glu Phe Gly Tyr Gly Leu Ser Tyr Thr Thr
                645                 650                 655

Phe Lys Tyr Ser Asn Leu Gln Val Thr Pro Leu Asn Ala Pro Lys Tyr
            660                 665                 670

Thr Pro Ala Ser Gly Lys Thr Asp Pro Ala Pro Ser Phe Gly Gln Pro
            675                 680                 685

Gly Ser Ala Ser Gln Tyr Val Phe Pro Arg Thr Leu Asn Arg Ile Tyr
        690                 695                 700

Glu Tyr Ile Tyr Pro Trp Leu Asn Ser Thr Asn Leu Arg Glu Ser Ser
705                 710                 715                 720

Gly Asp Pro Asp Tyr Gly Met Lys Ala Ser Ala Tyr Ile Pro Ala Gly
                725                 730                 735

Ala Thr Asp Gly Ser Ala Gln Glu Leu Leu Pro Ala Ser Gly Ala Pro
            740                 745                 750

Gly Gly Asn Pro Gly Leu Tyr Asp Glu Leu Phe Arg Val Ser Ala Thr
            755                 760                 765

Ile Thr Asn Thr Gly Lys Val Ala Gly Asp Glu Val Pro Gln Leu Tyr
        770                 775                 780

Val Ser Leu Gly Gly Pro Asn Asp Pro Lys Val Val Leu Arg Asn Phe
785                 790                 795                 800

Asp Arg Ile Asn Ile Ala Pro Gly Gln Ser Val Glu Trp Thr Thr Thr
                805                 810                 815

Leu Thr Arg Arg Asp Leu Ser Asn Trp Asp Val Ala Ala Gln Asp Trp
            820                 825                 830

Val Ile Ser Lys Tyr Pro Lys Thr Val Tyr Val Gly Ser Ser Ser Arg
        835                 840                 845

Lys Leu Pro Leu Gln Ala Thr Leu Pro Gln Val Asn
850                 855                 860

<210> SEQ ID NO 7
<211> LENGTH: 2465
<212> TYPE: DNA
<213> ORGANISM: Talaromyces leycettanus

<400> SEQUENCE: 7

```
atgcttgctg agcaaatctt cctgagtgtt ctggcagcag ccgtcactgt ccaggcctat      60
ggcttcggcg gctctggctg ggacgccgct tatggcagag caaaggctgc gctgaacaag     120
ctcaaccaga ccgagaaggt tggtatcgtc accggtgtca agtggatggg cggcccttgt     180
gttggcaaca cctacaagcc cagttcgatt gactacccct ctctgtgttt gcaagactct     240
cctctcgggg tgcgttttgc caaccctgtg actgccttcc cggctggtat caacgccggc     300
gccacatggg atagatctct catcaacgcc cgtggtgcgg ccatgggcgc tgaggccaag     360
ggcctcggtg tgaacgtcca gcttggcccc gtcgctggtc ctctcggcaa gaatcccaat     420
agtggcagaa tctgggaagg gttctcgaat gatccctatc tcagcggtgt tgcgatggag     480
gaaaccatcg ccggaatgca aggatctggt gtgcaggcct cgccaaggt acgtggatct      540
cgttcttgca acatgtacga tctgttgagg gctgacacga tacctgaatc tatagcacta    600
tattggtaac gagcaagagc acaaccgtga aaccatcagc tccaacatcg atgaccgcac    660
tctgcacgag ctctacgtct ggccgttcat gaacgccgtc aaggccaacg tcgcctccgt    720
catgtgctcg tacaacaagg tcaatggttc ctggtcctgt gagaatgatg ctcttctcaa    780
cggtctgttg aagactgagc tcggattccc cggatacatc atgagcgatt ggaacgcgca    840
gcacaccacg gtcaacagcg ccaactcggg tctcgatatg accatgcctg gcagtgactt    900
caacaaccct cctggcagca tctactgggg gcccaacctc gaagccgccg tcgccaatgg    960
ctccgttccg cagtcccgtt tggacgacat ggtcactcgt atccttgcgt cttggtactt   1020
ggttggccag gatgagggct acccaccggt cgccttcagc tcctggaatg gcggcaaggc   1080
caatgttgac gtgacgggcg atcacaagag cgtcgtcaga gctgtggctc gtgactctat   1140
cgttcttctg aagaacgaca ataacgcttt gcctctgcgc aagcccaaga gcctcgcgat   1200
catcggccag gatgcaactg tcaaccctgc cgggcccaac gcttgctctg atcgcggctg   1260
cgacaccggt actctcgcca tgggttgggg cagtggtacc gctcagttcc cagtgagtcg   1320
tcccattgca acttccacag gagcgaccgg tgactaacaa gcacctagta catcgtcggc   1380
cctctcgatg ctatccagtc tcaggctgcc gctgatggca ctaacatcac caccagcacg   1440
accgatgata ccaccgcggc agcttctgca gccgcctccg ccggaaccgc catcgtcttc   1500
atcaactccg actctggtga agggtaagcc cgggcgtcaa gatcctcgta cagatgggcc   1560
cgcatcgcta acattctaca gttacatcac cgtcgagggc aacgctggtg accgcaacaa   1620
cctcgacccc tggcacaacg gcaacgagct cgtccaggcc gttgcggctg tgaacaagaa   1680
tgtcattgtc gttgtccaca gcgtcggtcc cgtgatcttg gagactatcc ttgcacagcc   1740
caacgtcaag gccattgtgt ggcccggtct ccctggacaa gagagcggca atgccctggt   1800
cgatgttctg tacggctcca cctcccccag cggcaagttg ccctatacca ttgccaagca   1860
gttcagcgac tatggcacca cctggacgac ctccctggtc gatgacttca ccgagggtct   1920
gttcattgac taccgccact ttgacgagaa caacattact cccagatacg agttcggata   1980
cggcttgtgt tagtacttcc ttctctctct cgtagatcca tgctgtcttt gcaacgacac   2040
aaactgacat gataatagct tacaccacct tcaaatactc cgacctggac gtcaacgtcc   2100
aggcccgccc cggcgcagcc gaaggcccca tcgtcccgg cggcgtcaag gaacttttcg    2160
acaccgtcgg caccgtcacc gtcaccgtcc agaacagcgg caaggttgcc ggcgcggaag   2220
ttgcccagct gtacatcggc cttcccgact ctgcccgtc gacccctccc aagcagctca    2280
gaggattcca gaagttgcac ctcgcgcccg gccagagaga gggcgccact ttcgaactca   2340
```

```
cccgccgaga catcagctac tgggacgttc agcagcagaa gtgggttgtt cctagcggta    2400
cgttcaaggt ctatgttgga agctcgagca gggacattag ggagcaggga tctttccgta    2460
tttga                                                                2465
```

<210> SEQ ID NO 8
<211> LENGTH: 737
<212> TYPE: PRT
<213> ORGANISM: Talaromyces leycettanus

<400> SEQUENCE: 8

```
Met Leu Ala Glu Gln Ile Phe Leu Ser Val Leu Ala Ala Val Thr
1               5                   10                  15

Val Gln Ala Tyr Gly Phe Gly Gly Ser Gly Trp Asp Ala Ala Tyr Gly
            20                  25                  30

Arg Ala Lys Ala Ala Leu Asn Lys Leu Asn Gln Thr Glu Lys Val Gly
        35                  40                  45

Ile Val Thr Gly Val Lys Trp Met Gly Gly Pro Cys Val Gly Asn Thr
    50                  55                  60

Tyr Lys Pro Ser Ser Ile Asp Tyr Pro Ser Leu Cys Leu Gln Asp Ser
65                  70                  75                  80

Pro Leu Gly Val Arg Phe Ala Asn Pro Val Thr Ala Phe Pro Ala Gly
                85                  90                  95

Ile Asn Ala Gly Ala Thr Trp Asp Arg Ser Leu Ile Asn Ala Arg Gly
            100                 105                 110

Ala Ala Met Gly Ala Glu Ala Lys Gly Leu Gly Val Asn Val Gln Leu
        115                 120                 125

Gly Pro Val Ala Gly Pro Leu Gly Lys Asn Pro Asn Ser Gly Arg Ile
    130                 135                 140

Trp Glu Gly Phe Ser Asn Asp Pro Tyr Leu Ser Gly Val Ala Met Glu
145                 150                 155                 160

Glu Thr Ile Ala Gly Met Gln Gly Ser Gly Val Gln Ala Cys Ala Lys
                165                 170                 175

His Tyr Ile Gly Asn Glu Gln Glu His Asn Arg Glu Thr Ile Ser Ser
            180                 185                 190

Asn Ile Asp Asp Arg Thr Leu His Glu Leu Tyr Val Trp Pro Phe Met
        195                 200                 205

Asn Ala Val Lys Ala Asn Val Ala Ser Val Met Cys Ser Tyr Asn Lys
    210                 215                 220

Val Asn Gly Ser Trp Ser Cys Glu Asn Asp Ala Leu Leu Asn Gly Leu
225                 230                 235                 240

Leu Lys Thr Glu Leu Gly Phe Pro Gly Tyr Ile Met Ser Asp Trp Asn
                245                 250                 255

Ala Gln His Thr Thr Val Asn Ser Ala Asn Ser Gly Leu Asp Met Thr
            260                 265                 270

Met Pro Gly Ser Asp Phe Asn Asn Pro Gly Ser Ile Tyr Trp Gly
        275                 280                 285

Pro Asn Leu Glu Ala Ala Val Ala Asn Gly Ser Val Pro Gln Ser Arg
    290                 295                 300

Leu Asp Asp Met Val Thr Arg Ile Leu Ala Ser Trp Tyr Leu Val Gly
305                 310                 315                 320

Gln Asp Glu Gly Tyr Pro Pro Val Ala Phe Ser Ser Trp Asn Gly Gly
                325                 330                 335

Lys Ala Asn Val Asp Val Thr Gly Asp His Lys Ser Val Val Arg Ala
```

```
                340             345             350
Val Ala Arg Asp Ser Ile Val Leu Leu Lys Asn Asp Asn Asn Ala Leu
            355                 360                 365

Pro Leu Arg Lys Pro Lys Ser Leu Ala Ile Ile Gly Gln Asp Ala Thr
        370                 375                 380

Val Asn Pro Ala Gly Pro Asn Ala Cys Ser Asp Arg Gly Cys Asp Thr
385                 390                 395                 400

Gly Thr Leu Ala Met Gly Trp Gly Ser Gly Thr Ala Gln Phe Pro Tyr
                405                 410                 415

Ile Val Gly Pro Leu Asp Ala Ile Gln Ser Gln Ala Ala Asp Gly
                420                 425                 430

Thr Asn Ile Thr Thr Ser Thr Thr Asp Asp Thr Thr Ala Ala Ala Ser
            435                 440                 445

Ala Ala Ala Ser Ala Gly Thr Ala Ile Val Phe Ile Asn Ser Asp Ser
        450                 455                 460

Gly Glu Gly Tyr Ile Thr Val Glu Gly Asn Ala Gly Asp Arg Asn Asn
465                 470                 475                 480

Leu Asp Pro Trp His Asn Gly Asn Glu Leu Val Gln Ala Val Ala Ala
                485                 490                 495

Val Asn Lys Asn Val Ile Val Val His Ser Val Gly Pro Val Ile
            500                 505                 510

Leu Glu Thr Ile Leu Ala Gln Pro Asn Val Lys Ala Ile Val Trp Pro
            515                 520                 525

Gly Leu Pro Gly Gln Glu Ser Gly Asn Ala Leu Val Asp Val Leu Tyr
        530                 535                 540

Gly Ser Thr Ser Pro Ser Gly Lys Leu Pro Tyr Thr Ile Ala Lys Gln
545                 550                 555                 560

Phe Ser Asp Tyr Gly Thr Thr Trp Thr Thr Ser Leu Val Asp Asp Phe
                565                 570                 575

Thr Glu Gly Leu Phe Ile Asp Tyr Arg His Phe Asp Glu Asn Asn Ile
            580                 585                 590

Thr Pro Arg Tyr Glu Phe Gly Tyr Gly Leu Ser Tyr Thr Thr Phe Lys
        595                 600                 605

Tyr Ser Asp Leu Asp Val Asn Val Gln Ala Arg Pro Gly Ala Ala Glu
            610                 615                 620

Gly Pro Ile Val Pro Gly Gly Val Lys Glu Leu Phe Asp Thr Val Gly
625                 630                 635                 640

Thr Val Thr Val Thr Val Gln Asn Ser Gly Lys Val Ala Gly Ala Glu
                645                 650                 655

Val Ala Gln Leu Tyr Ile Gly Leu Pro Asp Ser Ala Pro Ser Thr Pro
            660                 665                 670

Pro Lys Gln Leu Arg Gly Phe Gln Lys Leu His Leu Ala Pro Gly Gln
        675                 680                 685

Arg Glu Gly Ala Thr Phe Glu Leu Thr Arg Arg Asp Ile Ser Tyr Trp
690                 695                 700

Asp Val Gln Gln Gln Lys Trp Val Val Pro Ser Gly Thr Phe Lys Val
705                 710                 715                 720

Tyr Val Gly Ser Ser Ser Arg Asp Ile Arg Glu Gln Gly Ser Phe Arg
                725                 730                 735

Ile

<210> SEQ ID NO 9
<211> LENGTH: 49
```

```
<212> TYPE: DNA
<213> ORGANISM: Artificial
<220> FEATURE:
<223> OTHER INFORMATION: PCR primer

<400> SEQUENCE: 9
acacaactgg ggatccacca tggcgttcaa atccggctat atgacgtgg              49

<210> SEQ ID NO 10
<211> LENGTH: 52
<212> TYPE: DNA
<213> ORGANISM: Artificial
<220> FEATURE:
<223> OTHER INFORMATION: PCR primer

<400> SEQUENCE: 10
agatctcgag aagcttatta ccttccacct tgaacaccag agaagctata gc          52

<210> SEQ ID NO 11
<211> LENGTH: 58
<212> TYPE: DNA
<213> ORGANISM: Artificial
<220> FEATURE:
<223> OTHER INFORMATION: PCR primer

<400> SEQUENCE: 11
acacaactgg ggatccacca tggctcgact atcatatctc atgtcgttcg ttttctgt    58

<210> SEQ ID NO 12
<211> LENGTH: 45
<212> TYPE: DNA
<213> ORGANISM: Artificial
<220> FEATURE:
<223> OTHER INFORMATION: PCR primer

<400> SEQUENCE: 12
agatctcgag aagcttacta cacggcaagg cattgtgctc caacc                  45

<210> SEQ ID NO 13
<211> LENGTH: 44
<212> TYPE: DNA
<213> ORGANISM: Artificial
<220> FEATURE:
<223> OTHER INFORMATION: PCR primer

<400> SEQUENCE: 13
acacaactgg ggatccacca tgaggcttgg gtggcttgag gtgg                   44

<210> SEQ ID NO 14
<211> LENGTH: 45
<212> TYPE: DNA
<213> ORGANISM: Artificial
<220> FEATURE:
<223> OTHER INFORMATION: PCR primer

<400> SEQUENCE: 14
agatctcgag aagcttatca gttgacctga ggcaatgtcg cctgc                  45

<210> SEQ ID NO 15
<211> LENGTH: 52
<212> TYPE: DNA
<213> ORGANISM: Artificial
<220> FEATURE:
<223> OTHER INFORMATION: PCR primer

<400> SEQUENCE: 15
```

```
acacaactgg ggatccacca tgcttgctga gcaaatcttc ctgagtgttc tg            52
```

<210> SEQ ID NO 16
<211> LENGTH: 52
<212> TYPE: DNA
<213> ORGANISM: Artificial
<220> FEATURE:
<223> OTHER INFORMATION: PCR primer

<400> SEQUENCE: 16

```
agatctcgag aagcttatca aatacggaaa gatccctgct ccctaatgtc cc            52
```